US009931161B2

(12) United States Patent
Willis

(10) Patent No.: US 9,931,161 B2
(45) Date of Patent: Apr. 3, 2018

(54) COAXIAL DUAL FUNCTION PROBE AND METHOD OF USE

(71) Applicant: AngioDynamics, Inc., Latham, NY (US)

(72) Inventor: Jeffrey R. Willis, Gansevoort, NY (US)

(73) Assignee: AngioDynamics, Inc., Latham, NY (US)

( * ) Notice: Subject to any disclaimer, the term of this patent is extended or adjusted under 35 U.S.C. 154(b) by 30 days.

(21) Appl. No.: 14/591,071

(22) Filed: Jan. 7, 2015

(65) Prior Publication Data

US 2015/0126922 A1    May 7, 2015

Related U.S. Application Data

(62) Division of application No. 13/150,586, filed on Jun. 1, 2011, now abandoned.

(51) Int. Cl.
*A61B 18/18* (2006.01)
*A61B 18/14* (2006.01)
(Continued)

(52) U.S. Cl.
CPC ...... *A61B 18/1487* (2013.01); *A61B 18/1477* (2013.01); *A61N 1/327* (2013.01); *A61B 17/3417* (2013.01); *A61B 17/3421* (2013.01); *A61B 18/1815* (2013.01); *A61B 90/36* (2016.02); *A61B 2018/00434* (2013.01); *A61B 2018/00517* (2013.01);
(Continued)

(58) Field of Classification Search
CPC ............ A61B 17/3417; A61B 17/3421; A61B 18/1477; A61B 18/1487; A61B 18/1815; A61B 19/52; A61B 2018/00434; A61B 2018/00517; A61B 2018/00577; A61B 2018/00583; A61B 2018/00613; A61B 2018/00791; A61B 2018/00916; A61B 2018/00982; A61B 2019/04
See application file for complete search history.

(56) References Cited

U.S. PATENT DOCUMENTS 6,193,715 B1 * 2/2001 Wrublewski ....... A61B 18/1402
 604/22
6,241,725 B1 * 6/2001 Cosman ............. A61B 18/1477
 600/41

(Continued)

*Primary Examiner* — Michael Peffley
*Assistant Examiner* — Amanda Zink
(74) *Attorney, Agent, or Firm* — Zachary F. Madonna, Esq.

(57) ABSTRACT

An energy delivery probe for use in tissue ablation and method of use is presented. The energy delivery device has at least a first energy delivery member and a second energy delivery member that have handle members positioned along a longitudinal axis, each handle member having a proximal and distal end. The distal end of the first handle member is releasably coupled to the proximal end of the second handle member and a portion of each member is defined in a coaxially surrounding relationship to each other along the longitudinal axis. The method of using the probe involves identifying a tissue to be ablated, providing the energy delivery probe, inserting at least a portion of the energy delivery probe into the identified tissue, delivering electrical energy through the energy delivery probe to the identified tissue, and ablating the identified tissue such that at least a first ablation zone is formed.

14 Claims, 17 Drawing Sheets

(51) Int. Cl.
*A61N 1/32* (2006.01)
*A61B 18/00* (2006.01)
*A61B 17/34* (2006.01)
*A61B 90/00* (2016.01)

(52) U.S. Cl.
CPC ............ *A61B 2018/00577* (2013.01); *A61B 2018/00583* (2013.01); *A61B 2018/00613* (2013.01); *A61B 2018/00791* (2013.01); *A61B 2018/00916* (2013.01); *A61B 2018/00982* (2013.01); *A61B 2090/0807* (2016.02); *A61B 2090/3966* (2016.02)

(56) References Cited

U.S. PATENT DOCUMENTS

| | | | |
|---|---|---|---|
| 7,582,058 B1* | 9/2009 | Miles | A61B 5/0492 600/202 |
| 7,918,852 B2* | 4/2011 | Tullis | A61B 18/1477 606/41 |
| 2007/0016185 A1* | 1/2007 | Tullis | A61B 18/1477 606/41 |
| 2008/0132884 A1* | 6/2008 | Rubinsky | A61B 18/1477 606/34 |
| 2010/0174170 A1* | 7/2010 | Razavi | A61B 5/042 600/371 |
| 2011/0112531 A1* | 5/2011 | Landis | A61B 17/2812 606/52 |

* cited by examiner

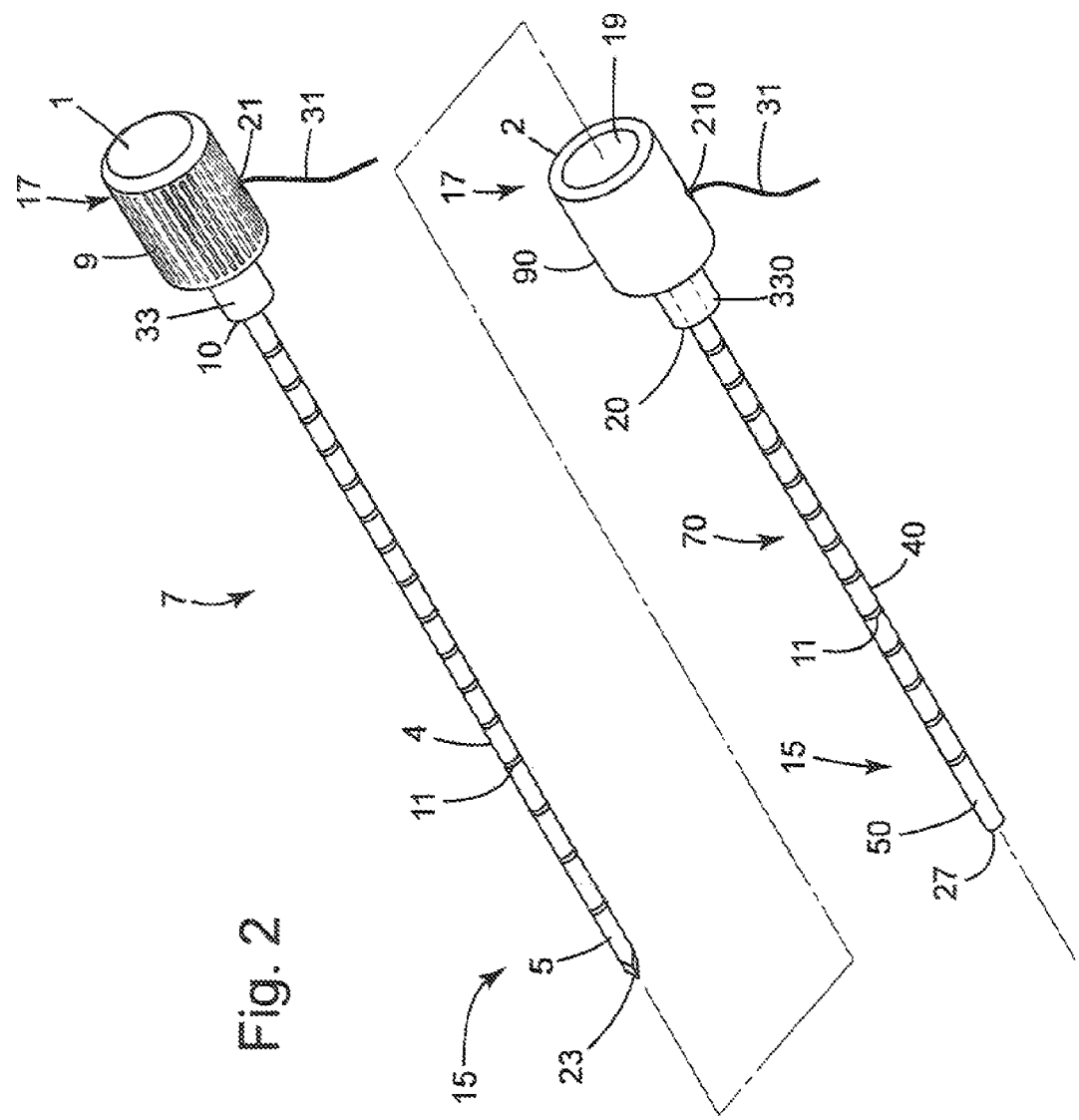

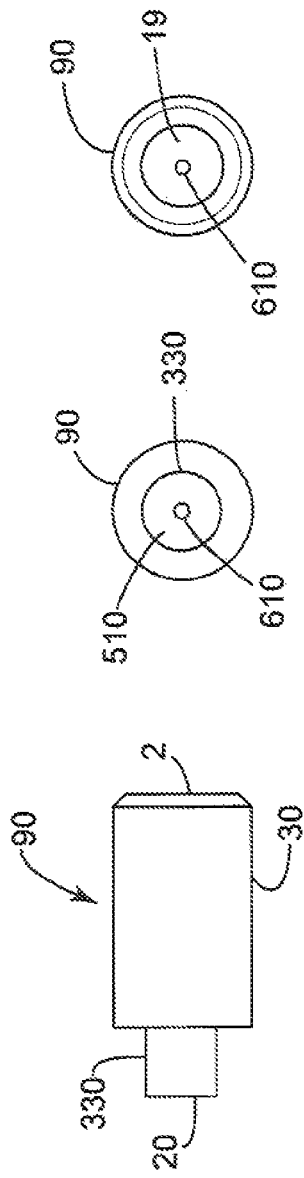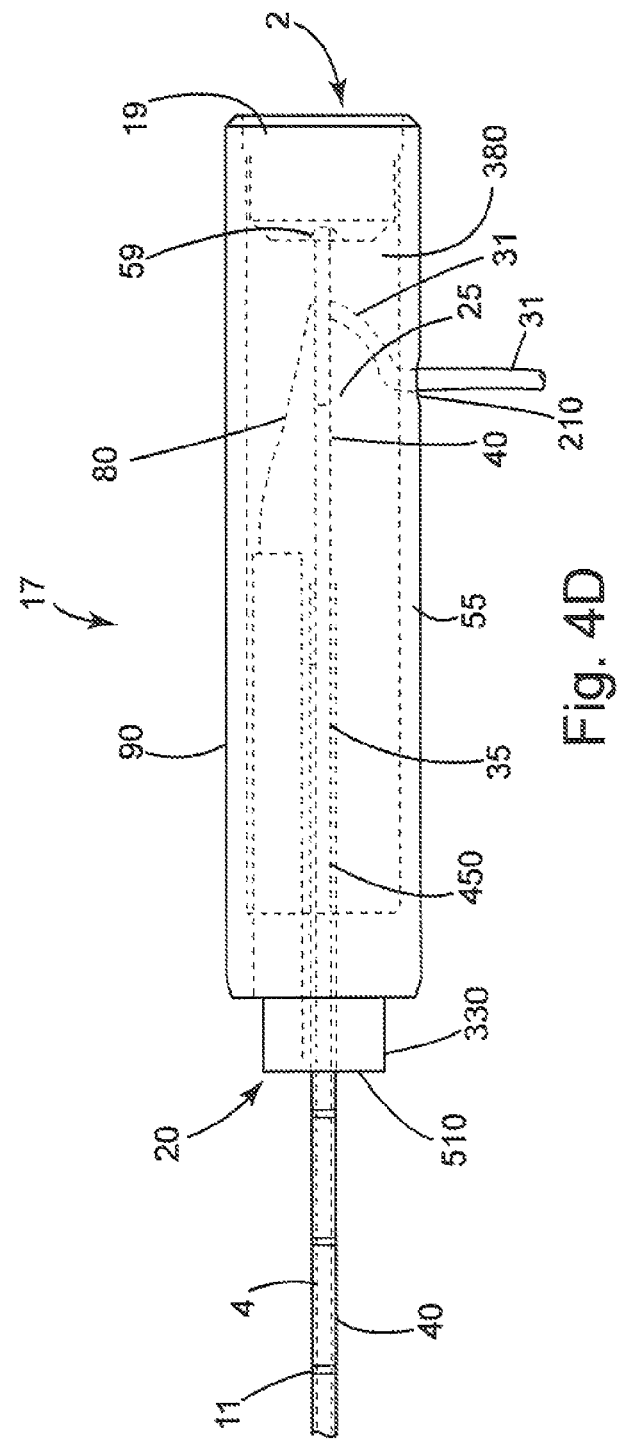

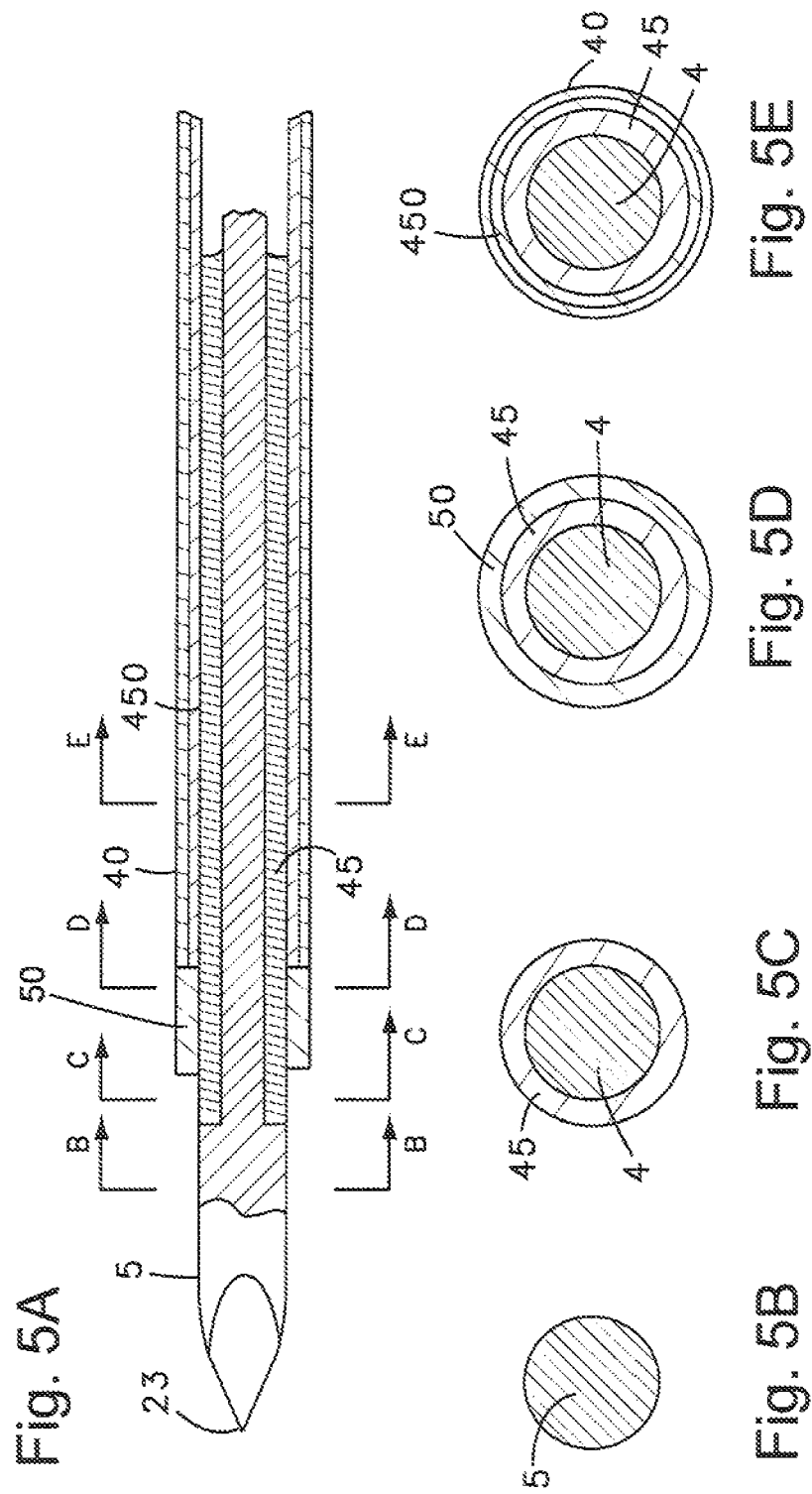

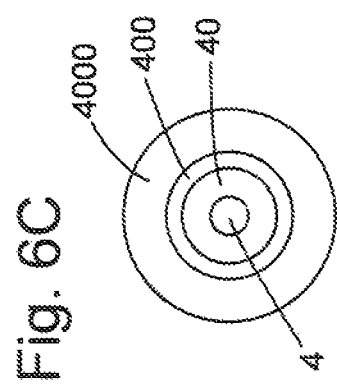
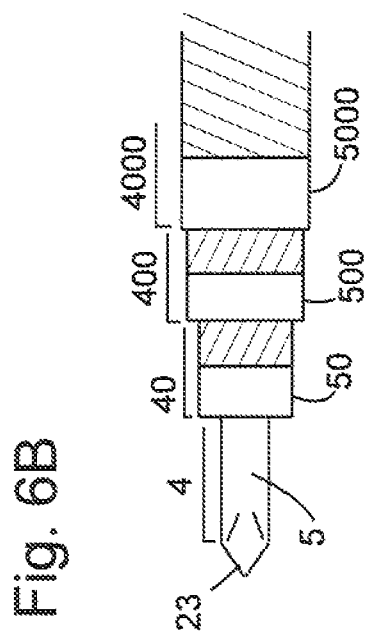

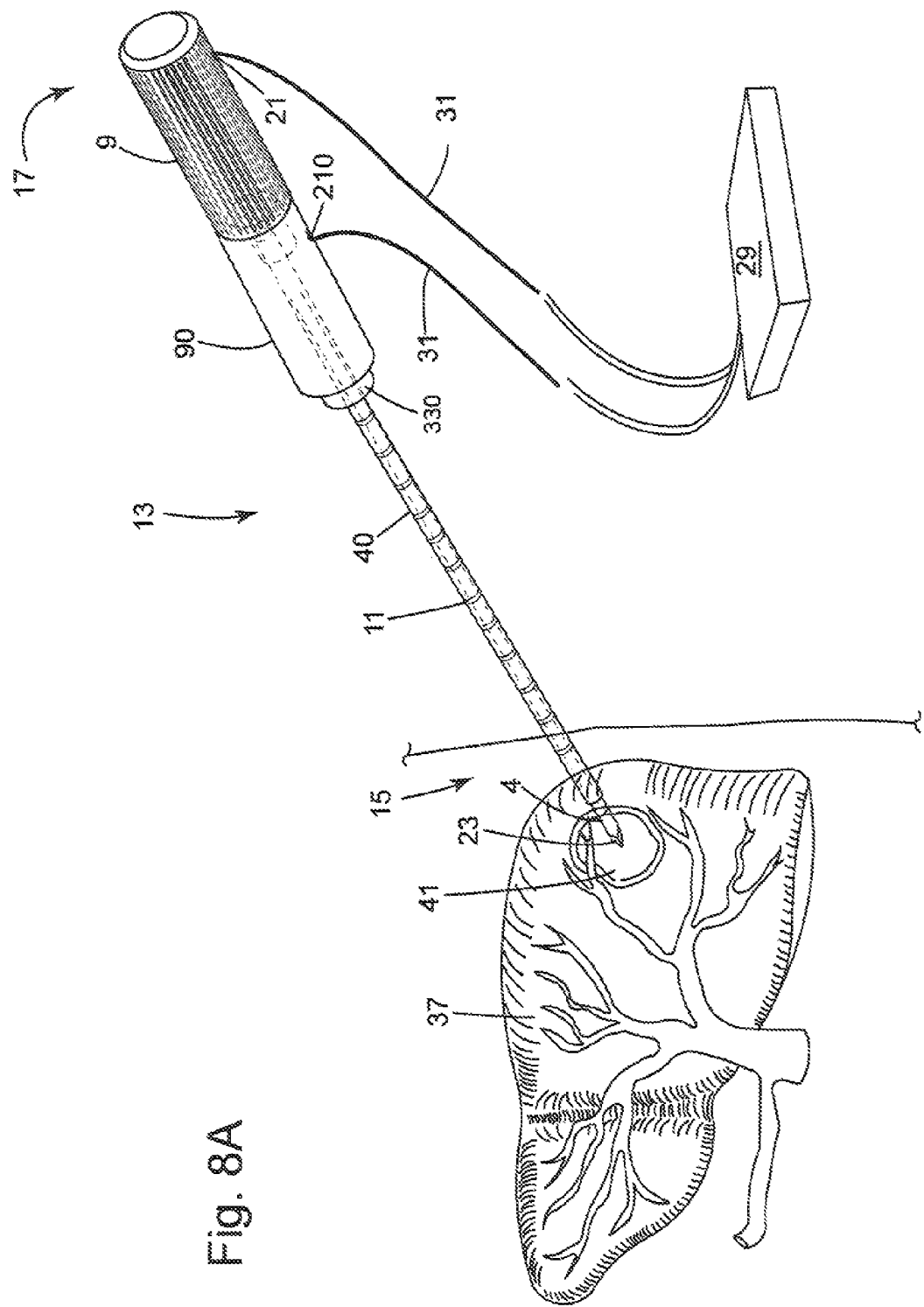

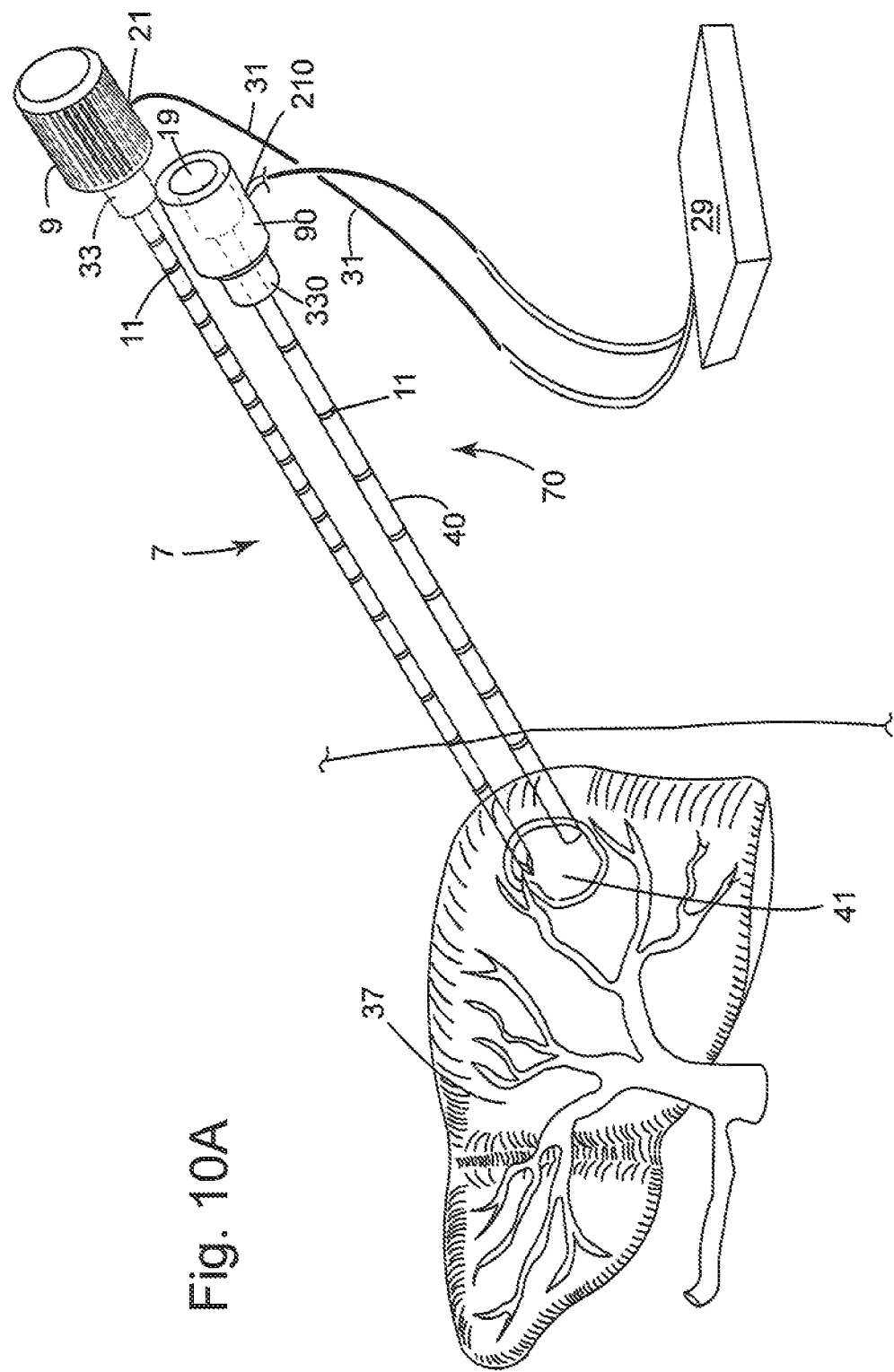

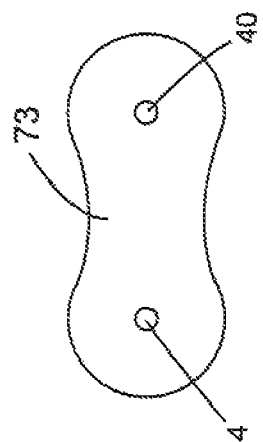
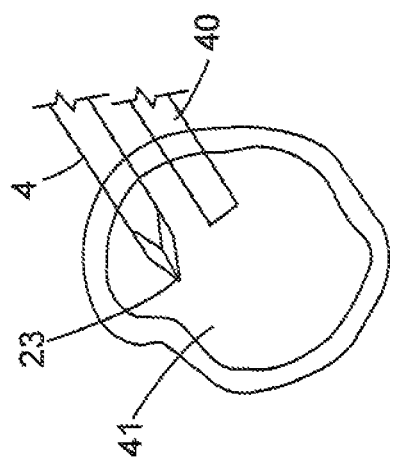

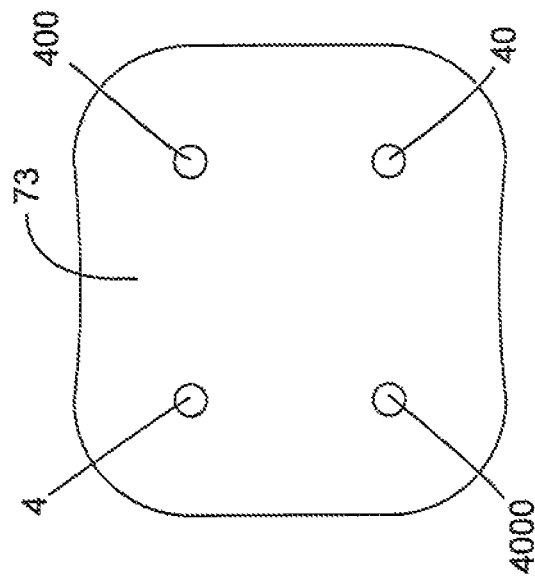
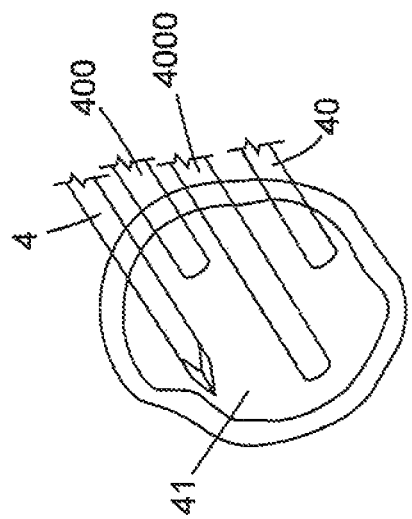

COAXIAL DUAL FUNCTION PROBE AND METHOD OF USE

CROSS REFERENCE TO RELATED APPLICATIONS

This application claims priority under 35 U.S.C. 119(e) to U.S. application Ser. No. 13/150,586, filed on Jun. 1, 2011.

BACKGROUND OF THE INVENTION

The present application relates generally to devices and methods for tissue treatment using Irreversible Electroporation (IRE). More specifically, the application relates to devices and methods for treatment of tissue through the application of pulsed electric fields that create nonthermal cellular effects and that can be applied at a level of sufficient strength so as to result in ablation of tissue.

The application of an electric field to transiently permeabilize cells is a method known as reversible electroporation. In reversible electroporation, membrane defects are created and later reseal, allowing a time when macromolecules can be introduced across the cell membrane. This has been used, for example, to insert genes into cells (electrogenetherapy), and to insert anti-cancer drugs into cells (electrochemotherapy). A primary goal of reversible electroporation is to lead to cellular defects that allow passage of macromolecules while still allowing cell survival.

Irreversible electroporation (IRE) is a method of applying electrical fields across tissue through a delivery of pulses that effectively result in membrane permeabilization and in cell necrosis. IRE has been discussed in Rubinsky et al., "Irreversible Electroporation: A New Ablation Modality—Clinical Implications," *Technology in Cancer Research and Treatment*, Vol. 6(1):37-48 (2007), which is incorporated herein by reference in its entirety.

Typically, during IRE treatment, needles of commercially available IRE probe devices are initially placed separately from each other in a parallel position with uniform spacing between each needle in order to perform a single ablation treatment. A limitation of such commercially available IRE probes is that such devices function primarily as either a bipolar probe device or a monopolar probe device, and there is typically very little, if any, cross-functionality between such devices, such that if a practitioner desires to use one device as a bipolar device and another device as a monopolar device, one electrosurgical device may have to be removed and replaced with a different device in order to switch between a bipolar and a monopolar treatment, thereby causing disruption to the patient and increased procedure time.

Another problem associated with current IRE devices is that during a single IRE ablation, a practitioner may desire to adjust the ablation volume of a target tissue while minimizing the potential disruption to a patient from the removal and reinsertion of all of the electrodes into the patient's tissue.

There exists a need in the art for an improved multi-probe ablation device that can function as a bipolar or monopolar device and a method of using such a device that will allow practitioners to alter the position of the electrodes in relationship to each other before, during, and after an ablation, with minimal disruption and discomfort to a patient, to generate multiple varied size ablations. An ablation device and method has not yet been proposed that would solve the problems described above, thereby avoiding the negative side effects of the current devices described above.

It is a purpose of the invention described herein to provide a dual function releasably coupled coaxial ablation device that can be used as a single energy delivery device or multiple energy delivery devices.

It is a purpose of the invention described herein to provide a dual function ablation device that can be used for either IRE or radiofrequency (RF) ablations.

It is a purpose of the invention described herein to provide a dual function ablation device that can be used for either bipolar or monopolar ablations.

It is a purpose of the invention described herein to provide a dual function ablation device that is configured to allow a practitioner to vary the electrode spacing in order to accommodate multiple ablations.

It is a purpose of this invention to provide a dual function ablation device that can be used to produce larger ablation volumes than are typically feasible using single electrode ablation devices.

Various other objectives and advantages of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention can be found in the Detailed Description of the Invention.

SUMMARY

A method of ablating tissue using an energy delivery probe device is provided herein. The method involves identifying a tissue to be ablated and providing an energy delivery probe that has at least a first energy delivery member that has a first handle member and a second energy delivery member that has a second handle member positioned along a longitudinal axis. Each of the handle members has a proximal end and a distal end. A portion of the distal end of the first handle member is coupled to a portion of the proximal end of the second handle member. The method further involves inserting at least a portion of the energy delivery probe into the identified tissue and delivering electrical energy through the energy delivery probe to the identified tissue in an amount sufficient to ablate the identified tissue such that at least a first ablation zone is formed.

An energy delivery probe for use in tissue ablation is provided herein. The energy delivery probe has at least a first energy delivery member having a handle member and a second energy delivery member having a second handle member disposed along a longitudinal axis, each handle member having a proximal end and a distal end. A portion of the distal end of the first handle member is coupled to a portion of the proximal end of the second handle member, and at least a portion of the first handle member and the second handle member are disposed in a coaxially surrounding relationship to each other along the longitudinal axis.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 2 illustrates a perspective view of first energy delivery member and a second energy delivery member of the energy delivery probe device of FIG. 1 in a disassembled state.

FIG. 4A illustrates a side view of the second energy delivery member handle of FIG. 2.

FIG. 4B illustrates a front end view of the second energy delivery member handle of FIG. 2.

FIG. 4C illustrates a back end view of the second energy delivery member handle of FIG. 2.

FIG. 4D illustrates a sectional view of the of the second energy delivery member handle of FIG. 2.

FIG. 5A illustrates an enlarged partial longitudinal sectional view of the distal end of the energy delivery device of FIG. 1.

FIG. 5B illustrates a cross-sectional view along lines B-B of the distal end of the energy delivery device of FIG. 1.

FIG. 5C illustrates a cross-sectional view along lines C-C of the distal end of the energy delivery device of FIG. 1.

FIG. 5D illustrates a cross-sectional view along lines D-D of the distal end of the energy delivery device of FIG. 1.

FIG. 5E illustrates a cross-sectional view along lines E-E of the distal end of the energy delivery device of FIG. 1.

FIG. 6B illustrates an enlarged side view of the distal end of the energy delivery probe of FIG. 6A.

FIG. 6C illustrates an enlarged end view of the energy delivery probe of FIG. 6A.

FIG. 8A illustrates a method of ablating a target tissue using the energy delivery probe device described herein.

FIG. 10A illustrates a perspective view of a method of use of the energy delivery probe of FIG. 8A.

FIG. 10B illustrates an enlarged view of the distal ends of the energy delivery probe bodies of FIG. 10A inserted into a target tissue.

FIG. 10C illustrates a top view of an ablation zone produced by the energy delivery probe of FIG. 8A.

FIG. 12B illustrates an enlarged view of the distal ends of the energy delivery members of FIG. 12A being inserted into a target tissue.

FIG. 12C illustrates a top view of an exemplary ablation zone that can be produced by the four probe array of energy delivery members of FIG. 12A inserted into a target tissue.

DETAILED DESCRIPTION OF THE INVENTION

Figure 1:
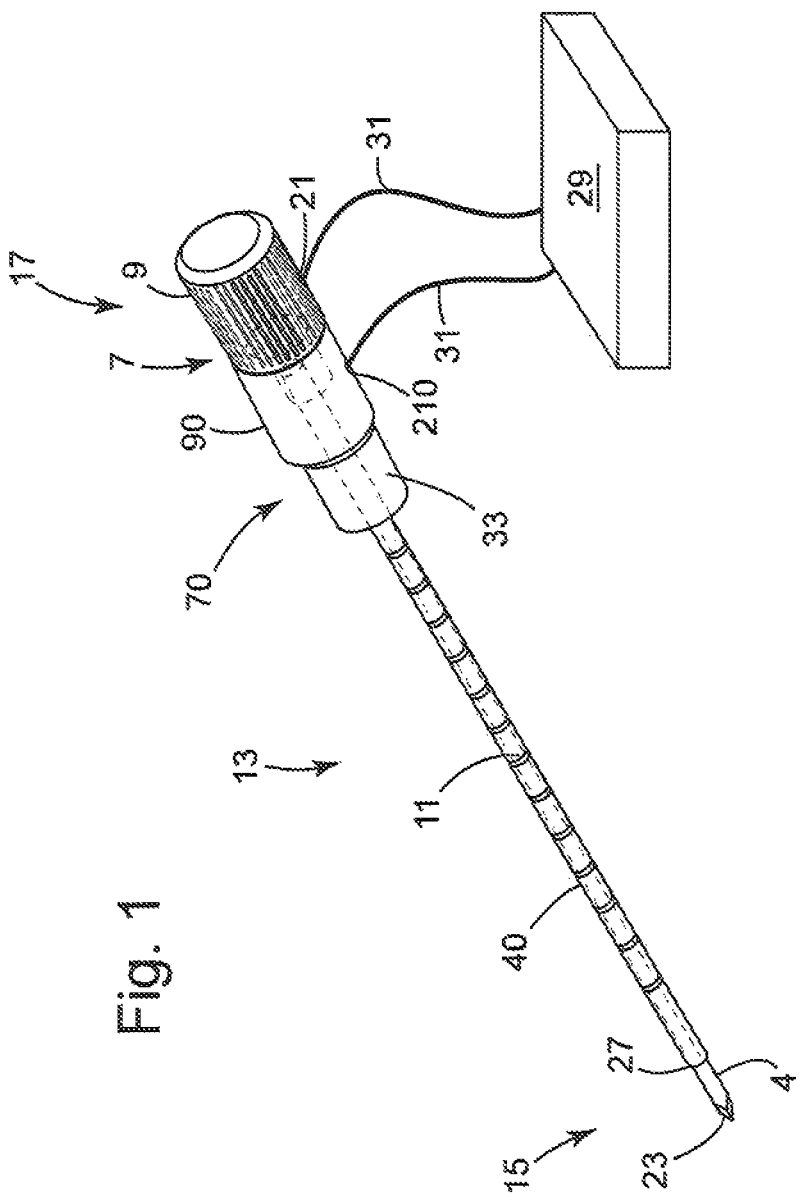
FIG. 1 illustrates a perspective sectional view of a first embodiment of an energy delivery probe device in an assembled state.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Ranges can be expressed herein as from "about" to one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, the words "proximal" and "distal" refer to directions away from and closer to, respectively, the tip of the energy delivery probe. The terminology includes the words above specifically mentioned, derivatives thereof, and words of similar import.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Examples provided herein, including those following "such as" and "e.g." are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

As used herein, "substantially", "generally", and other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic. "Optional" or "optionally" means that the subsequently described element, event or circumstance can or cannot occur, and that the description includes instances where said element, event or circumstance occurs and instances where it does not.

The term "ablation" is used herein to refer to either irreversible electroporation (IRE) ablations or radiofrequency ablation (RFA) ablations or both. "IRE ablation device" is used herein to refer to any of the devices described herein that can be used for IRE ablations. "RFA devices" can be used herein to refer to any of the devices described herein that can be used for RF ablations. All dimensions herein are exemplary, and one of ordinary skill in the art will recognize that other dimensions possible.

The term "radio frequency" or "RF" refers to an electrical current that alternates the poles in the radio frequency range (extending from below 3 kHz to about 300 gigahertz). "Activate", "activatable", or "activation", in the context of activating a distal end structure, e.g., electrode, refers to the application of a stimulus to the structure that is effective to ablate tumor tissue in contact with the structure. Such activation can include RF, microwave, or electrical current applied to an electrode or current applied to a resistive heating element, such as a tip or electrode.

Referring now in detail to the drawings, in which like reference numerals indicate like parts or elements throughout the several views, in various embodiments, presented herein is an exemplary ablation device and method of using the ablation device.

FIGS. 1 through 5E illustrate one exemplary embodiment of an energy delivery probe 13 for use in treating a patient. The ablation probe 13 can be configured for tissue treatment, including, but not limited to, pulsed electric field ablation and electroporative ablation. More particularly, the energy delivery probe can be configured to deliver electrical energy to a target tissue in an amount sufficient to ablate a target tissue. In one embodiment, the electrical energy can be radiofrequency energy (RF) or electrical pulses sufficient to reversibly or irreversibly electroporate (IRE) the target tissue.

In one aspect, the probe 13 can be a bipolar probe, as described in U.S. patent application Ser. No. 12/437,843, filed May 8, 2009, and incorporated herein by reference in its entirety. The probe 13 has a proximal end 17, a distal end 15 and a longitudinal axis. At least a portion of the proximal end 17 of the probe 13 can be configured to be positioned outside of a human body. At least a portion of the distal end 15 of the probe 1 can be configured to be inserted into at least a portion of a human body, such as, but not limited to, a target tissue.

The energy delivery probe 13 can comprise at least two probe bodies or energy delivery members 7, 70. More particularly, the probe 13 can comprise a first elongated energy delivery member 7 and a second elongated energy delivery member 70. Each of the energy delivery members 7, 70 has a proximal end and a distal end. In one aspect, each of the first and second energy delivery members 7, 70 comprises a handle member 9, 90 that can be positioned at the proximal end 17 of the probe 13. The proximal end 17 of the probe 13 and the proximal end of the handles 9, 90 are referred to herein interchangeably herein.

In one aspect, at least a portion of the distal end of the first handle member 9 of the first energy delivery member 7 can be operatively and releasably coupled to at least a portion of the proximal end of the second handle member 90 of the second energy delivery member 70. This allows the probe bodies 7, 70 to be connected via a snap fit relationship. In another aspect, although not shown, the first handle member 9 of the first energy delivery member 7 and the second handle member 90 of the energy delivery member 70 can be connected via an interlocking mechanism such as, but not limited to, a threaded male to female interlocking mechanism. Other mechanisms for attaching the energy delivery members 7, 70 include a luer fitting, a valve, a toughy-bourst connector, a swage fitting, or other adaptors and medical fittings known in the art. The connection is also referred to herein as a connecting structure and may include tubing, fittings, couplings, or any fastening suitable for releasably connecting the first handle 9 and the second handle 90 of the first and second energy delivery members. In other embodiments, the ablation device 13 can comprise more than two probe bodies 7, 70. In one embodiment, when handles 9, 90 are connected, they can have substantially equal outer diameters. One of ordinary skill in the art will recognize that other configurations can be used.

The energy delivery probe 13 further comprises at least one electrode. The probe 13 can comprise electrodes 4, 40, each having a proximal end and a distal end. Electrode 40 can be a cannula, and electrode 4 can be a trocar. Thus, electrode 4 and trocar 4 can be used interchangeably herein, and electrode 40 and cannula 40 can be used interchangeably herein. Each of the trocar and the cannula comprise a proximal end and a distal end 17 and 15, which ends are used interchangeably herein with the proximal and distal ends 17, 15 of the energy delivery probe 13. The first and second energy delivery members, the electrodes 4, 40, and the handles 9, 90 extend along the longitudinal axis of the energy delivery probe 13 and can be operatively and permanently coupled to the energy delivery members 7, 70, respectively. The electrodes 4, 40 can be configured to be operated in monopolar or bipolar modes, and may be capable of switching between the two modes.

In the assembled state, at least a portion of the electrodes 4, 40 are positioned within a portion of the probe bodies 7, 70 such that a portion of the electrodes 4, 40 extend into and are operatively coupled to a portion of handles 9, 90. In one exemplary embodiment, the trocar electrode 4 can be from about 13 gauge to about 15 gauge (1.828 mm to 1.449 mm) in size, depending on the desired treatment or a patient's anatomy. The trocar electrode 4 can have a uniform diameter throughout its longitudinal length. The working length of the trocar 4 can be between about 10 cm and about 25 cm. The working length of the trocar electrode 4 is defined from a point just distal of the distal end of the handle 9 to the distal tip 23 of the trocar, depending on the size of the target tissue to be ablated and a patient's anatomy.

The distal tip 23 can be sharp such that it is capable of piercing tissue. Tip 23 can have a beveled profile to enable or facilitate percutaneous application of probe 13. Alternatively, the tip 23 can have a blunt tip. In other embodiments, the tip 23 can be of any shape known in the art such that it is adequately configured to perform energy release, including, but not limited to, minimizing or preventing damage to surrounding cellular structures as well as increasing the effectiveness of energy release or the efficiency or the precision of treatment. In certain embodiments the tip 23 can have a bullet-shape or a bullet-nosed shape. In other embodiments the tip 23 can have rounded planes, it can be spherical or non-spherical in nature, or it can be ovoid in shape. The tip 23 can be utilized with multiple energy release forms and can be utilized as part of the energy delivery probe 13 for electroporation, thermal or non-thermal irreversible electroporation, radiofrequency ablation, thermal electric heating, and traditional heating methods with electrodes using direct current or alternating current.

Cannula 40 can be configured for receiving a portion of trocar 4. The cannula 40 functions as an electrode as well as a sleeve to house a portion of the first electrode 4. Thus, in the assembled state, at least a portion of electrode 4 of first probe body 7 is positioned within a portion of the cannula 40 of the second probe body 70. At least a portion of the first probe body or energy delivery member 7 and the second probe body or energy delivery member 70 are positioned in a coaxially surrounding relationship to each other. At least a portion of electrodes 4, 40 are positioned in a coaxially surrounding relationship to each other.

The first electrode 4 is axially slidable along the longitudinal axis of the second electrode 40 up to the point where the handles 9, 90 are operatively connected to each other. At least a portion of electrode 4 can be disposed within a portion of electrode 40 such that it extends distally of electrode 40. Tip 23 of the first electrode 4 can extend beyond the distal tip 27 of the second electrode 40 by about 7 mm when the first and second handles 9, 90 are securably interlocked.

At least one of the electrodes 4, 40 can comprise at least one index marker, such as, but not limited to, at least one depth marking 11, positioned along the outer surface of at least one of the electrodes 4, 40. The depth markings 11 can be fixed in place and equi-distantly positioned from one another. The depth markings 11 can be used to aid a practitioner in gauging the depth of deployment and ablation of the probe 13. In one aspect, the markers 11 can be radiopaque markers coated on the outer surfaces of the electrodes for visualization purposes.

The energy delivery probe 13 described herein can be configured to have sufficient probe rigidity to maximize the stability of the positioned probe, minimize inadvertent movements of the probe, and minimize device failure. In certain examples, the energy delivery probe 13 can be about 22 gauge in size or greater, while other embodiments can be 16 gauge or greater. In one aspect, the device can be scalable to fit the type of tissue being treated as well as a patient's individual anatomy. The probe 13 may be designed as disposables or for repeated uses. In one aspect, the probe 13 can be comprised of the same or different compositions, and can be independently comprised of one or more electrically conductive materials, including one or more metals and alloys thereof, such as various grades of stainless steel. The probe 13 can be comprised of a non-conductive material such as, but not limited to, polyimide or PEEK (polyether ether ketone).

Each of the probe bodies 7, 70 can be operatively coupled at the proximal end 17 of the probe 13 to a therapeutic energy or power source 29, including a high voltage pulse generator through at least one cable 31. The electrodes can be coupled to the power source and/or a ground pad electrode, in monopolar mode, via an insulated wire. The coupling can also be made using a coaxial cable, thereby allowing for coupling of one or both electrodes to the power source 29 as a ground pad electrode. The electrodes are coupled to the power source 29 such that power may be independently applied to each electrode. The electrodes may be independently coupled to the power source where the power source has independent channels, or the electrodes may be coupled to a multiplexer that controls power to each of the electrodes separately.

The power source 29 can be, but is not limited to, an RF source, electrical energy source, microwave source, short wave source, high voltage pulse generator, laser source and the like. The generator 29 is configured for supplying energy to the probe 13 in a controlled manner. The energy delivery source 29 can be capable of delivering energy that is selected from the group comprising: radiofrequency (RF) energy, microwave energy, and electrical energy. One skilled in the art will recognize that other types of energy delivery are contemplated herein. In one aspect, the energy source 29 can further comprise a switching means for switching between monopolar and bipolar delivery of energy to the electrodes. Such generators are commercially available from AngioDynamics, Inc. (Latham, N.Y.) and can include, but are not limited to, AngioDynamics' RITA® 1500X RF generator or NanoKnife® generator.

Referring to FIG. 2, the first and second energy delivery members 7, 70 can be disconnected from each other upon application of a force applied by a user, thereby allowing a user to slidably remove trocar electrode 4 from cannula electrode 40. Alternatively, the trocar 4 can be inserted into the cannula 40 and the handles releasably connected using a means for locking the handles 9, 90, described above.

Each of the handles 9, 90 can have a proximal end 1, 2 a distal end 10, 20, respectively, an outer surface, and an inner cavity. Optionally, at least a portion of at least one of the handles 9, 90 can comprise a ribbed outer surface. This surface can provide a user a means for gripping, manipulating, and positioning the handles 9, 90. Handle 9 comprises a male fitting 33 that extends toward the distal tip 23 of the trocar electrode 4. Trocar 4 can extend from an interior of the handle 9 to distal tip 23. A first voltage delivery region 5 is disposed near the distal tip 23 of the trocar 4, and a second voltage delivery region 50 is disposed near the distal end of the cannula 40.

In one aspect, the trocar or electrode 4 can be solid without any lumens or openings. Alternatively, in additional embodiments, either of the trocar 4 or cannula 40 can have at least one lumen or channel (not shown) that extends along the longitudinal axis of the probe 13 as well as openings at its distal end that are in communication with the longitudinal lumen or lumens. The at least one channel can be used to deliver or withdraw fluids. The channel can extend from the proximal end 17 of the energy delivery probe 13 to the distal end 15 of the energy delivery probe. The channel can be used for the delivery or withdrawal of substances, including, but not limited to at least one of infusion media, solutions or suspensions containing one or more therapeutic as well as diagnostic agents, chemotherapeutic agents, or other drugs, hydrogels, colloidal suspensions containing nanoparticles as well as microparticles, cryogenic fluids, ablative fluids, such as, but not limited to, ethanol or high salt, high molecular weight drugs, or chemotherapeutic drugs, and saline, which may be injected through the lumen and can be ejected from the end of the needle tip 23. In one aspect, an electrically conductive fluid can be supplied at or near the target tissue 41 through a portion of the energy delivery probe 13. In certain embodiments, substances can be delivered to increase the conductivity of the tissue, and in others, can be delivered to increase the efficiency of ablation. In other embodiments the substances can be released to alter the conductivity of tissue. In other embodiments the energy delivery probe 13 can be capable of extracting substances selected from the group consisting of tissue, fluids, medium, solutions, suspensions, therapeutics, hydrogels, nanoparticles, and microparticles. In other embodiments, the energy delivery probe 13 can comprise thermal sensors that can be positioned within a portion of the energy delivery probe 13.

Handle 90 comprises a female opening 19 that is defined in the proximal end of the handle 90. In the assembled state, at least a portion of male fitting 33, described above, can be inserted into at least a portion of opening 19 in order to form a snap-fit or interference fit connection. Each of the handles comprises at least one opening 21, 210 through which at least one cable 31 can extend. A portion of the cable 31 is positioned within at least a portion of the handles 9, 90 such that the at least one cable 31 is adjacent to the proximal end 17 of the probe 13 and extends outwardly from the proximal end 17 of the handle 9 through openings 21, 210 in each of the bodies 7, 70. The placement of the cables 31 through openings 21, 210 in the outer surface of the handles 9, 90 of each of the bodies 7, 70 is advantageous because it allows the probe bodies 7, 70 to be stacked and releasably connected to each other without the cables interfering with the connection or the placement of the electrodes.

In one embodiment, at least a portion of the trocar 4 and cannula 40 can be rigid if the probes are IRE probes, but flexible or semi-flexible if the probe is an RF probe. The rigid body and sharp tip 23 of the trocar 4 can be useful for penetrating target tissues, especially large, hard tumors. A "tumor" refers to an abnormal lump or mass of tissue. Tumors can be benign (not cancerous) or malignant (cancerous).

Figure 3A:
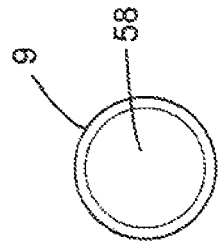
FIG. 3A illustrates a side view of the first energy delivery member handle of FIG. 2.
Figure 3B:
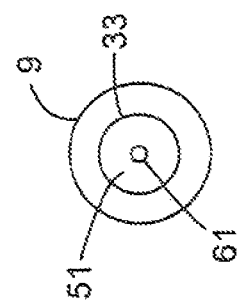
FIG. 3B illustrates a front end view of the first energy delivery member handle of FIG. 2.

FIGS. 3A through 3D illustrate first handle 9 of the probe body 7. The handle can be from about 1 inch to about 2 inches in length and about 0.5 to about 0.75 inches in diameter. One of ordinary skill in the art will recognize that other configurations can be used. The handle 9 comprises a main body 3 having a proximal end 1, a distal end 10, and a male fitting 33 that is permanently attached to at least a portion of the handle 9. Each of the main body 3 and the male fitting 33 comprise an outer surface and a cavity. The male fitting 33 has a length and diameter that is smaller than the length and diameter of the main body 3. In one exemplary embodiment, the main body 3 can be ribbed, as described above. As illustrated in FIG. 3B, the distal portion 10 of male fitting 33 can comprise an opening 61 defined therein a distal face 51 of the male fitting 33 such that it is sized to allow an outer surface of the electrode or trocar 4 extend through the opening 61. The opening 61 faces substantially in a distal direction toward the tissue piercing tip 23 of the energy delivery probe 13. In the assembled configuration, the male fitting 33 of the handle 9 can be inserted into opening 19 of the handle 90 such that the handles 9, 90 form a snap-fit, interference fit, or threaded connection, as described above. The handles 9, 90 can be attached and removed from each other upon application of a force applied by a user.

Figure 3C:
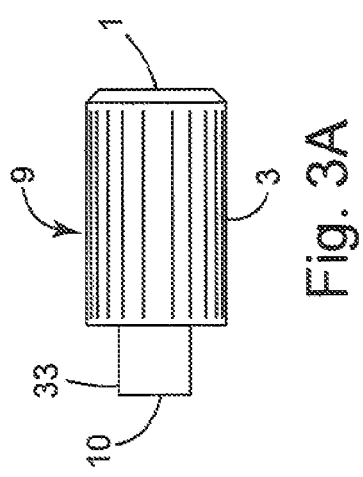
FIG. 3C illustrates a back end view of the first energy delivery member handle of FIG. 2.
Figure 3D:
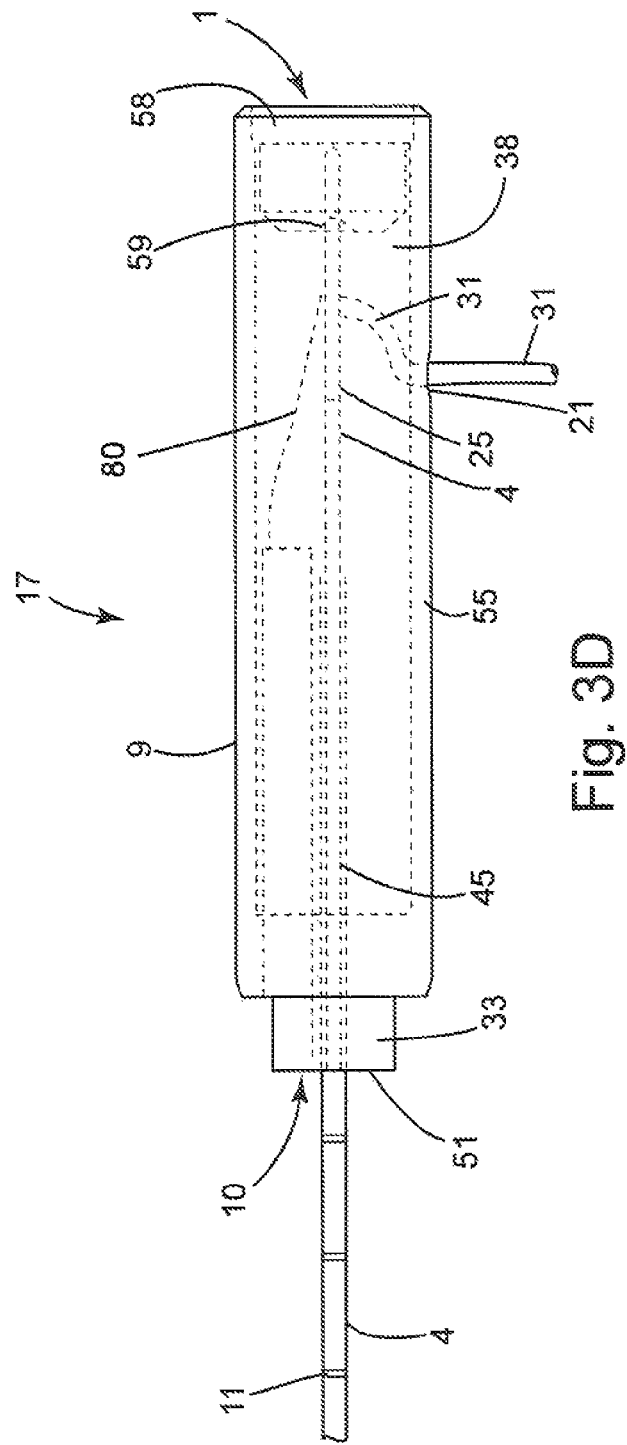
FIG. 3D illustrates a sectional view of the first energy delivery member handle of FIG. 2.

Referring to FIGS. 3C and 3D, handle 9 can include a proximal closing member, such as a plug 58, and a cavity 38. As illustrated in the enlarged view of the handle 9 in FIG. 3C, the trocar electrode 4 can extend proximally into cavity 38 and can terminate in a distal-facing recess 59 of plug 58. Plug 58 can be fixedly coupled to handle 9 to cap off cavity 38. As such, a portion of energy delivery probe 13 is fixedly coupled between at least opening 61 and plug 58 within handle 9. Adhesives or other non-limiting bonding techniques can be used to render probe 13 immovable relative to handle 9. Although opening 61 has a substantially circular shape, one of ordinary skill in the art will recognize that the opening 61 can have other shapes as well, including, but not limited to, elliptical or crescent shaped.

Opening 21 can be defined in the outer surface of the handle 9 such that it is configured for receiving at least one cable 31 from cavity 38. The at least one cable 31 can be electrically coupled to proximal portion 25 of the trocar electrode 4, thus also to voltage delivery region 5, through lead wire 80. As described below, the electrode can further comprise at least one electrically insulative layer 45. Non-limiting examples of coupling methods include soldering, lead wire wounding, electrically conductor lugs, and combinations thereof. The bonding joints are placed within body portion 55 during assembly.

In one aspect, cavity 38 can be at least partially filled with a flowable material, including but not limited to a liquid, semi-liquid, as well as a gel, and a hardening material, such as, but not limited to, at least one of a cross-linkable, polymerizable, or otherwise curable material, that is electrically insulating, such as epoxy, to secure and immobilize the various components within body portion 7, as well as provide electrical insulation among the various components and between the components and a device operator. The components within body portion 7, including cables 31, and lead wire 80, in addition to other components, are immobilized relative to handle 9. The handle design is configured to prevent ingression of fluids into handle 9.

FIGS. 4A through 4D illustrate handle 90 of the probe body 70. The handle 90 comprises a proximal end 2, a distal end 20, a main body 30 and optionally, a male fitting 330 that is permanently attached to at least a portion of the handle 90 and extends distally toward the distal end 15 of the probe 13. Each of the main body 30 and the male fitting 330 comprise an outer surface and a cavity. The male fitting 330 has a length and diameter that is smaller than the length and diameter of the main body 30. In one aspect, the main body can be ribbed, as described above. Alternatively, the handle 90 can be non-ribbed. In the two probe body configuration, it is not necessary for the handle 90 to be ribbed because typically the first handle 9 will be removed and reinserted into the target tissue, while the handle 90 remains stationary. The male fitting 330 can comprise an opening 610 that can be positioned within the distally facing surface 510 of the male fitting 330 such that it is sized to allow an outer surface of the cannula 40 to extend through the opening 610. The opening 610 faces substantially in a distal direction toward the distal end 15 of the energy delivery probe 13. Opening 210 can be defined in the outer surface of the handle 90 and can be configured for receiving cables 31, which can extend into cavity 380. At least one of the cables 31 can be electrically coupled to proximal portion 25 of the trocar electrode 4, thus also to voltage delivery region 50, through lead wire 80.

Referring to FIG. 4C and the enlarged view illustrated in FIG. 4D, handle 90 is substantially identical to handle 9, except that handle 90 is not sealed by plug 58. Rather, handle 90 comprises opening 19 at the proximal end of the handle 90. Energy delivery probe 13 can extend proximally into cavity 380 and terminate through distal-facing recess 59 of opening 19. As described below, the cannula can comprise at least one electrically insulative layer 450.

Referring to FIGS. 5A through 5E, an electrically insulative layer can be coaxially positioned around at least a portion of at least one of the trocar electrode 4 and cannula electrode 40. At least a portion of the inner surface of the cannula 40 and the outer surface of the trocar 4 can be electrically insulated or separated from each other by a first electrically insulating member or insulative sleeve 45. The at least one electrically insulating member or insulation sleeve 45 can separate the at least two voltage delivery regions 5, 50 in a manner sufficient to prevent electrical shorting or arcing between voltage delivery regions 5, 50, which can adversely affect treatment efficiency as well as efficacy.

FIG. 5A illustrates an enlarged sectional view of the distal portion of the probe device 13, and FIGS. 5B-5E illustrate several cross-sectional views highlighting the orientation of electrically conducting and insulating portions that can be arranged in certain embodiments so as to provide the probe 13 with a substantially similar diameter throughout its length. Probe 13 can comprise at least two voltage delivery regions 5 and 50, which can be electrically insulated from each other and disposed along at least a portion of the length of the body portions of probe 13. In one aspect, the probe 13 can comprise more than two voltage delivery regions. First energy delivery member 7 can include a distal portion for voltage delivery that includes voltage delivery region 5 and that tapers toward distal tip 23. The voltage delivery region 5 can have a uniform diameter along a majority of its length. Second energy delivery member 70 can include a voltage delivery region 50 that is positioned at or near the distal tip of the cannula 40, as illustrated. The plurality of voltage delivery regions 5, 50 can be independently or inter-dependently configured to be energized with a predetermined polarity, as long as at least two of the voltage delivery regions are configured to be energized with opposite polarities. It has been observed that when voltage delivery region 5 is configured to be positively, or cathodically energized while voltage delivery region 50 is configured to be negatively, or anodically energized, electrical arcing at tip 23 occurred less than if the polarity is reversed, i.e., with region 5 being negative or anodic, while region 50 being positive or cathodic. The energy delivery probe 13 can enable safe delivery of pulsed voltage, including 1 kV or greater, without endangering the patient or causing device malfunctions such as shorting or arcing, thereby enhancing the efficiency and efficacy of treatment.

In one aspect, the electrically insulating layer 45 can be approximately the same length as each of two voltage delivery regions 5, 50. One of ordinary skill in the art will recognize that the voltage delivery regions and the insulating regions can be varied in length. For example, any of the voltage delivery regions can be longer or shorter than any of the insulating layers. In one non-limiting example, electrically insulating region 45 can have a length of approximately 8 mm that is substantially the same as or greater than that of voltage delivery region 5, which is approximately 7.5 mm, and voltage delivery region 50, which is approximately 7 mm. In another exemplary embodiment, the exposed portion of each of the electrodes 4, 40, as shown, can be 7 mm in length, and the two probes 7, 70 can be spaced from each other by about 15 mm. In one aspect, the bare electrode 4 extends beyond the distal most tip of the cannula 40 for about 7 mm.

In one embodiment, first insulation sleeve 45 can comprise a polyamide material. The insulation sleeve 45 can be semi-rigid. The first insulative sleeve 45 can extend from at least a portion of the handle 9, 90 at the proximal end of the cannula 4 and trocar 40 to within about 0.25 to about 0.5 inches from the tip 23 of the trocar 4. The trocar 40 can comprise a recessed portion in which the first insulation sleeve 45 may be positioned. The first insulation sleeve 45 is positioned in a coaxially surrounding relationship around at least a portion of an exterior of the trocar 4 such that the insulation is flush with the greatest dimension of the outer diameter of the trocar 4, and can be permanently fixed in place, as illustrated in FIG. 5A. In this aspect, the trocar 4 can have a substantially equal outer diameter along the entire length of the trocar 4. In other embodiments, first insulation sleeve 45 can have a diameter that is substantially the same as or smaller or larger than those of voltage delivery region 5.

A distal end portion of the insulation sleeve 45 of the trocar 4 can be removed such that the trocar 4 is bare. The bare distal tip of the electrode/trocar 4 provides an energy delivery region 5. One of ordinary skill in the art will recognize that the insulation sleeve 45 can be adjusted along the length of the trocar 4 to any desired position. All or some portion of the insulation sleeves 45 may be adjustably positioned so that the length of the energy delivery region 5 of trocar 4 can be varied. The thickness of the insulation 45 can vary, depending on whether the probe is an IRE probe or an RF probe. The insulation thickness may be varied because the operating voltage and currents of IRE and RF devices can be significantly different.

Cannula 40 coaxially surrounds trocar 4 in the assembled configuration, as illustrated in FIGS. 5A through 5E. Cannula 40 comprises an insulation sleeve 450. The insulative sleeve 450 can extend from the handle 90 at the proximal end of the device to within about 0.25 to about 0.5 inches from the tip 23 of the cannula 40. The cannula 40 can comprise a recessed portion in which the insulation sleeve 450 may be positioned. The insulation sleeve 450 is positioned in a coaxially surrounding relationship around at least a portion of an exterior of the cannula 40 such that the insulation 450 is flush with the greatest dimension of the outer diameter of the cannula 40 and can be permanently fixed in place. Thus, the cannula 40 can have a substantially equal outer diameter along the entire length of the cannula 40. A distal end of the insulation sleeve 450 at the distal end of the cannula 40 can be removed such that the cannula 40 is bare to form energy delivery region 50. As illustrated in FIG. 5E, trocar electrode 4 is coaxially surrounded by a first electrically insulative layer 45, and a second electrically insulative layer 450, which layers electrically separate electrode 4 from cannula 40.

Each of electrically insulating members 45, 450 can include one or more layers of the same or different electrically non-conductive materials. One of ordinary skill in the art will recognize that more than one insulation layer can be used in the energy delivery probe 13 described herein. Use of multiple layers as well as coatings to form the electrically insulating members reduces or eliminates the occurrence of pin holes and damage occurring during the manufacturing process. In certain examples, electrically insulating member 45, or a layer thereof, can be comprised of the same or different electrically non-conductive materials, or can be fabricated as a single-piece tubular structure rather than separate pieces to simplify the assembly of probe 13. The single-piece, electrically insulating member can have a distal cylindrical portion that is greater in outer diameter and wall thickness than a proximal cylindrical portion. Suitable electrically non-conductive materials can have a dielectric strength of 10 MV/m or greater, such as 15 MV/m or greater, or 7 MV/m or greater.

Electrically non-conductive materials for electrically insulating members 45, 450 can include polyethylene terephthalate, polyimides, polyamides, polyamide-imides, singly and in combinations of two or more. Electrically insulating members 45, 450 can have a uniform outer diameter. Thickness of electrically insulating members 45, 450 can be 0.05 inches or less. In alternative embodiments, members 45, 450 can be 0.03 inches or less in diameter. A central lumen passing through the distal and proximal portions of the single-piece electrically insulating member can have a substantially uniform diameter that is equal to or greater than the outer diameter of portion 25 of the trocar 4, cannula 40. Non-limiting methods of making a single electrically insulating piece that includes electrically insulating members 45, 450 can include extrusion, co-extrusion, molding, co-injection molding, and others known to one skilled in the art. Electrically insulating members 45, 450 can also be applied onto the outer surface of trocar 4, cannula 40, among other methods, by sliding on and shrink-wrapping one or more tubular structures, such as sleeves as well as tubing, of thermoplastics, as well as by forming one or more surface coatings, such as vapor deposition, spraying, dipping, or molding.

Each of voltage delivery regions 5, 50 can be independently or inter-dependently configured to be energized with a predetermined polarity, as long as at least two of the voltage delivery regions are configured to be energized with opposite polarities. In certain embodiments each of voltage delivery regions 5, 50 are electrically coupled to one of two cables 31 and one of two separate connectors (not shown), to be independently energized as well as polarized. In additional embodiments, voltage delivery region 5 is oppositely energized with respect to one or both of voltage delivery region 50. Optionally, although not illustrated, a spacing member can be coaxially disposed about electrically insulating member 45, as described in U.S. patent application Ser. No. 12/437,843, filed May 8, 2009, and incorporated herein by reference in its entirety.

In one aspect, although not illustrated, the probe 13 can further comprise at least one electrode array, as described in U.S. Pat. No. 6,932,814, incorporated herein by reference in its entirety. The trocar 40 can be coupled to a plurality of electrode arrays. In one embodiment, the energy delivery probe can also include a plurality of electrode arrays, each electrode having a proximal portion and a distal portion. The plurality of arrays can be at least partially positioned within at least one of the electrode trocars or cannulas such that it is adapted to be deployed radially away from the probe 13 and into a target tissue. In one aspect, such arrays can be deployed when the trocar and/or cannula is inserted into the tissue. The plurality of electrode arrays is adapted to receive electrical treatment energy from an energy source. The electrode arrays can be slidably disposed within a portion of the lumen of the elongate trocar 40 and deployable therefrom at a predetermined radius of curvature. The electrode arrays can be configured for passage through a plurality of openings that can be positioned in the outer wall of the trocar 40. The arrays can be comprised of a shape memory material, such as, but not limited to, Nitinol, stainless steel, and other suitable materials. The electrode arrays can have a pre-curved, non-linear shape that is biased to assume a desired configuration when advanced into a target tissue or region of tissue. At least a part of a distal portion of each deployed electrode array can be constructed to be structurally less rigid than the trocar 40. Each of the arrays can comprise an energy delivery surface that is capable of delivering energy to the tissue from energy source 29. The collective size of the deployed energy delivery surfaces is sufficient to create a volumetric ablation zone between the deployed electrodes when sufficient energy is delivered from the energy source to the ablation device. The electrode arrays can be deployed from the sleeve to create the appropriate margins. The electrodes may be deployed to a desired depth in the tissue, or may be deployed step-wise to a maximum depth while delivering power.

Figure 6A:
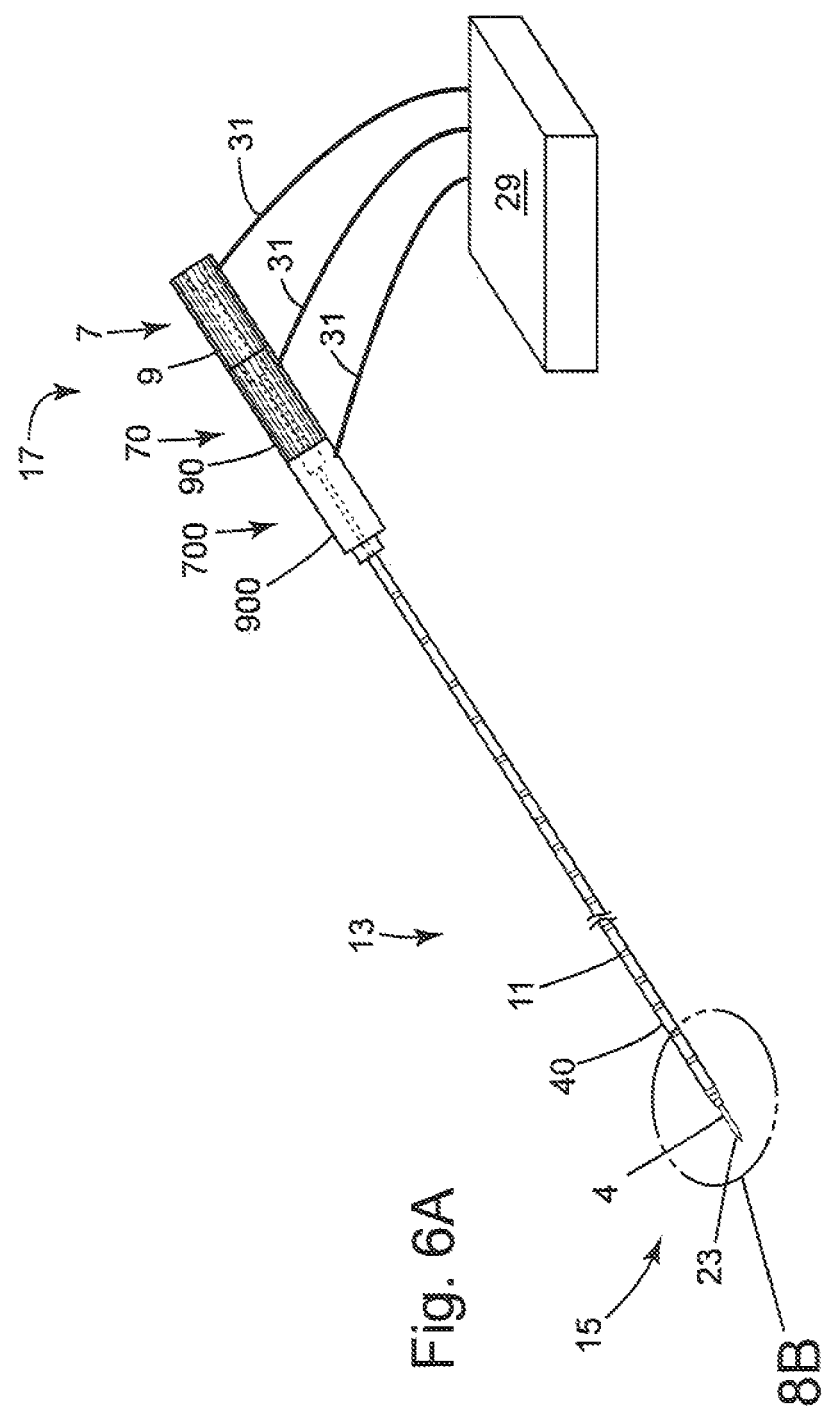
FIG. 6A illustrates a perspective view of another embodiment of the energy delivery probe.

In some embodiments, such as illustrated in FIGS. 6A through 12C, the energy delivery probe device 13 can comprise more than two probe bodies 7, 70, and can thus have more than two voltage delivery regions. For example, in one embodiment, the energy delivery probe 13 can comprise three or more energy delivery probes 7, 70, 700. Each of these probe bodies can comprise an energy delivery region 5, 50, 500, as illustrated in FIGS. 6A through 6C.

As illustrated in FIGS. 6B and 6C, and described above, the energy delivery probe 13 can comprise at least one layer of insulation, such that each of the energy delivery members are separated from each other by at least one electrically insulative layer. This configuration is a stacked or stepped configuration which can be useful for energy delivery treatment through at least one of the energy delivery members to a target tissue. As illustrated in the end view of FIG. 6C, trocar 4 of first probe body 7 can be coaxially surrounded by cannula 40 of probe body 70, which in turn, can be coaxially surrounded by cannula 400 of probe body 700, which in turn, can be coaxially surrounded by cannula 4000.

In one example, in the three probe embodiment, voltage delivery region 5 can be oppositely energized with respect to one or both of voltage delivery regions 50 and 500. In other embodiments, voltage delivery region 5 can be oppositely energized with respect to one or both of voltage delivery regions 50 and 500. In additional embodiments, only two of voltage delivery regions 5, 50 and 500 are oppositely energized at any given time, while the others are not energized. In certain embodiments, voltage delivery region 5 is cathodically energized, and in other embodiments region 50 is not energized. Certain embodiments include at least one of the following pattern of charge (polarization) for voltage delivery regions 5, 50, and 500: (+, −, −), (+, −, +), (+, +, −), (−, +, +), (−, +, −), (−, −, +), (+, −, X), (+, X, −), (−, +, X), (−, X, +), (X, +, −) and (X, −, +) where X represents no polarization. Any one of such patterns can be chosen exclusively throughout a procedure.

Alternatively, a combination of two or more of these patterns can be chosen in a predetermined series, randomly, or manually for any one or more portions of a procedure. In various embodiments, voltage delivery regions can be independently polarized as well as independently energized so as to ensure that a circuit is formed for current movement from any of the voltage delivery regions to any of the voltage delivery regions. In certain embodiments a cathodic polarization in the voltage delivery region including the tip 23, at the distal end of the probe device 13, will be energized such that current flows from the tip 23 to a voltage delivery region 5 independently charged anodically that is not at the tip 23 and is closer to the proximal half of the probe 13, closest to the distal portion of the handle 9, than to the tip 23. In certain embodiments where multiple probes are utilized together, independently energizing and independently polarizing can be used to ensure current flows from any voltage delivery region on one probe to any voltage delivery region on another probe, at any point along the length of the first or second energy delivery members containing a voltage delivery region.

FIGS. 7 through 12C illustrate methods of using various embodiments of the energy delivery probe 13 described herein. In one aspect, the energy delivery probe 13 described herein can be used with an electrical treatment planning software, such as, but not limited to, that provided by AngioDynamics, Inc. (with the NanoKnife® irreversible electroporation system), described in U.S. patent application Ser. No. 12/751,845, filed Mar. 31, 2010 and Ser. No. 12/751,854, filed Mar. 31, 2010, respectively, which applications are incorporated by reference herein in their entireties.

Figure 7:
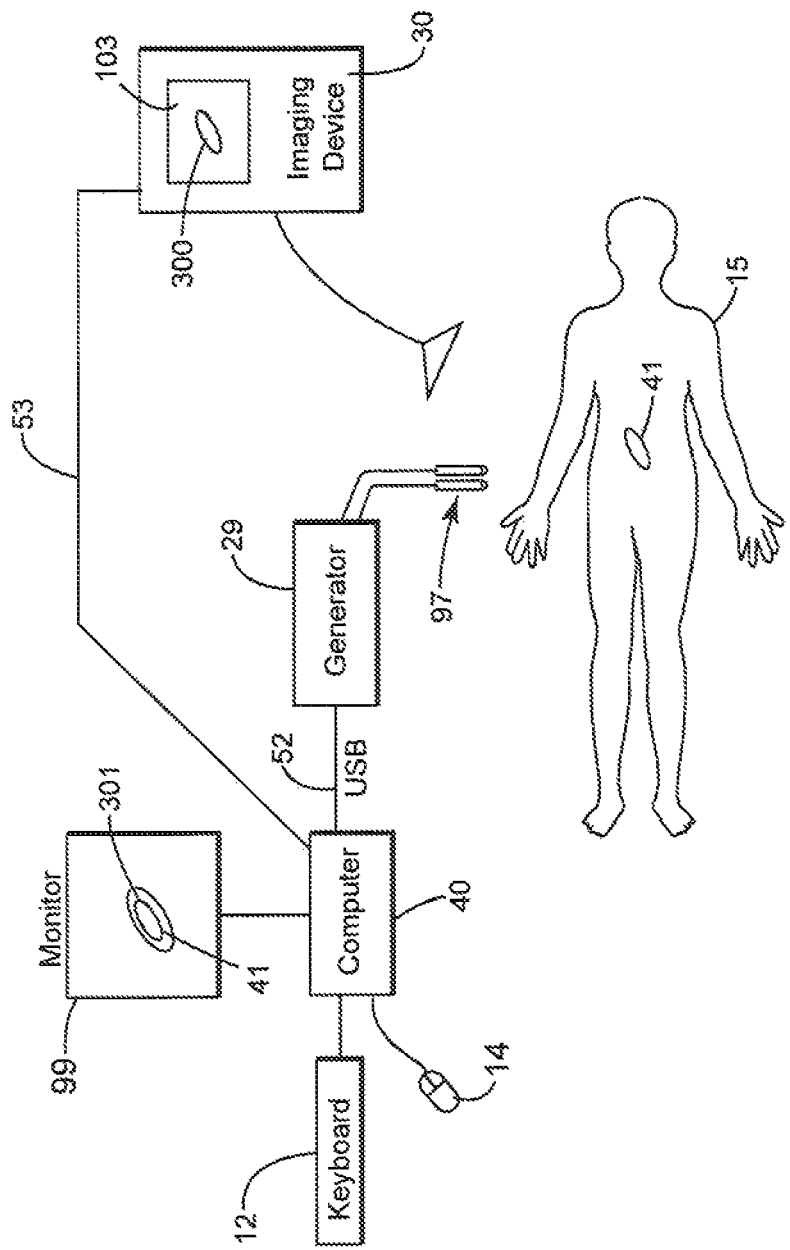
FIG. 7 illustrates several components that are used with the energy delivery probe device to treat a patient during a method of treatment.

Exemplary components that can be used with the method of the present invention are illustrated in FIG. 7. As described above, one or more probes 13 can deliver therapeutic energy and are powered by a voltage pulse generator 29 that generates high voltage pulses as therapeutic energy such as pulses capable of irreversibly electroporating the target tissue 41. In the embodiment shown, although two receptacles 97 are shown, the voltage pulse generator 29 can include six separate receptacles for receiving up to six individual energy delivery members which can be adapted to be plugged into a respective receptacle. The receptacles can each be labeled with a number in consecutive order. In other embodiments, the voltage pulse generator 29 can have any number of receptacles for receiving more or less than six probes.

As described above, each probe 13 can include either a monopolar electrode or bipolar electrodes having two electrodes separated by an insulating sleeve. In one embodiment, if the probe 13 includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 29 can be connected to a treatment control computer 40 having input devices such as keyboard 12 and a pointing device 14, and an output device such as a display device 99 for viewing an image of a target treatment area 300 such as a target tissue 41 or target tissue 41 surrounded by a safety margin 301. The therapeutic energy delivery device 13 is used to treat a target tissue 41 inside a patient 15. An imaging device 30 includes a monitor 103 for viewing the target tissue 41 inside the patient 15 in real time. Examples of imaging devices 30 include ultrasonic, CT, MRI and fluoroscopic devices as are known in the art.

The treatment system can also include computer software, such as treatment control module (not shown), which assists a user to plan for, execute, and review the results of a medical treatment procedure, as will be discussed in more detail below. For example, the treatment control module assists a user to plan for a medical treatment procedure by enabling a user to more accurately position each of the energy delivery members of the therapeutic energy delivery device 13 in relation to the target tissue 41 in a way that will generate the most effective ablation zone(s). The treatment control module can display the anticipated ablation zone(s) based on the position of the probes and the treatment parameters. The treatment control module can display the progress of the treatment in real time and can display the results of the treatment procedure after it is completed. This information can be used to determine whether the treatment was successful and whether it is necessary to re-treat the patient.

The dimensions of the target tissue 41 can be determined from viewing it on the monitor 103 of the imaging device 30, such as an ultrasonic imaging device and using known methods to calculate the dimensions from the image generated from the imaging device 103. The dimensions of the target tissue 41 can be inputted into a program (not shown). A safety margin can be selected at an input box (not shown) which will surround the entire target tissue 41 in three dimensions. According to the size of the safety margin that is selected, a target tissue treatment region 41 can be automatically calculated and displayed. In one embodiment, the safety margin value can be set to zero. For example, when treating a benign tumor, a safety margin may not be necessary.

A method of this invention can include choosing a probe type before treatment. In one aspect, a two probe type configuration can be chosen, as illustrated in FIG. 1. Other probe type selections can include between a three to a six probe configuration type selection. In one aspect, either a "six probe array 10 mm" or "six probe array 15 mm" can be selected, which refers to probe types utilizing a template which can be used to align a group of six needles in a fixed predetermined arrangement for treatment, wherein each pair of probes are equally spaced by 10 mm and 15 mm, respectively. Other probe device types having seven or more probes can be used. The user can select a probe type having a number of energy delivery members which will work most effectively to treat the specific size and shape of the target tissue 41 together with a safety margin 301.

After the user has selected a probe type on the "Probe Selection" screen, the user clicks on the "Next" button with a pointing device 14 to proceed to the "Probe Placement Process" screen described below. The probes can be positioned using a "Probe Placement Process" screen of one aspect of the invention. The screen (not shown), can illustrate a target tissue 41 according to the dimensions which were inputted, along with a safety margin 301, if any, that was previously inputted. In one example, the target tissue 41 can have a length of about 2.0 cm and a width of about 1.0 cm. In one example, the device selected on the "Probe Selection" screen can have a four probe configuration described in FIGS. 12A through 12C.

The target tissue 41 can be displayed near the center of an x-y grid (not shown) with the distance between two adjacent grid lines representing 1 mm. Each of the energy delivery members 7, 70 can be displayed in the grid, and each energy delivery member can be manually positioned within the grid by clicking and dragging the probe with a pointing device 14. At least one energy delivery member can be used as a fiducial or reference point, can be displayed on the grid, and can be used as a point of reference or a measure, as will be described below. The treatment control module can also display the distance, in centimeters (cm) from electrode 4 to a fiducial or reference point. This feature assists the user in placing the electrodes in preferred locations. This feature is especially beneficial if the imaging device 30 allows the calculation of measurements as is known in the art.

Figure 8B:
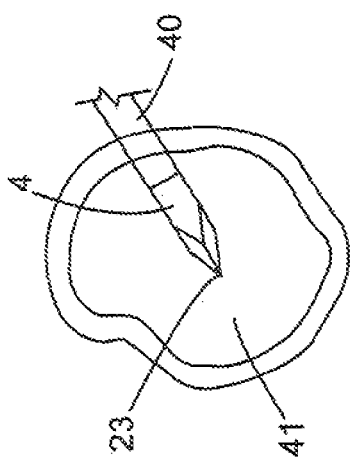
FIG. 8B illustrates an enlarged view of the method of ablating a target tissue of FIG. 8A.

Referring to FIG. 8A, after the probe bodies 7, 70 have been placed on the grid by a user to plan the treatment of target tissue 41 on the "Probe Placement Process" screen, a user inserts the energy delivery probe 13 into the patient according to a target tissue 41 that can be located within liver tissue 37, for example. The insertion of the probe 13 can be percutaneous, laparoscopic, endoscopic, as well as through natural orifices, including insertions related to orifice translumenal endoscopic surgery. One of ordinary skill in the art will recognize that other tissue types can be used as well, including, but not limited to, breast, prostate, and lung tissue. The energy delivery probe 13 can be suitable for treatment of conditions for various tissues, volumes, sizes and locations, including small to medium sized tissue volumes, and tissue volumes that are in close proximity to other non-targeted structures, such as, but not limited to, neuronal structures, vascular structures, duct structures, and collagen-rich structures. Non-limiting examples of tissue masses to which the devices of the present application are applicable include benign tissue masses such as benign prostate hyperplasia (BPH) and uterine fibroids, as well as benign or malignant masses such as cancers and tumors of various tissue types, including, but not limited to, prostate, uterine, lung, liver, kidney, brain, head/neck, bone, stomach, colon, and pancreas.

The energy delivery probe device 13 can be configured such that the probe 13 can be placed within or adjacent to the target tissue 41, enabling safe usage in situations where the tissue targeted for ablation is adjacent to critical as well as vital non-targeted structures, such as, but not limited to, the urethra or neurovascular bundles. Thus, the disclosed pulsed electric field ablation, when carried out under certain parameters and operating conditions, can selectively spare, including without damaging, destroying or denaturing, certain tissues and structures present within the ablation volume. Non-limiting tissues that can be selectably spared by the pulsed electric field ablation include nervous, vascular, duct, as well as collagen-rich tissues.

Therapeutic energy delivery devices disclosed herein can be designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art.

In one aspect, in the method of treatment, when the cannula 40 and a trocar 4 of the probe bodies 7, 70 are inserted into the tissue 41, the probe bodies 7, 70 are disposed in a releasably coupled position, also illustrated in FIG. 1. When the probe bodies 7, 70 are locked together, the assembled energy delivery probe 13 can function as a bipolar probe 13. After insertion of the energy delivery probe 13, the methods of the present application can involve positioning any one, two, or more than two of the voltage delivery regions along the probe 13 within or adjacent to the target tissue 41.

The positioning of the energy delivery members 7, 70 can be carried out under image guidance using one or more of the biological imaging modalities disclosed herein. In one example, the imaging can include, but not be limited to, ultrasound, CT, or MRI of the target tissue 41. The imaging can also include, but is not limited to, one, two, or more two-dimensional or three-dimensional biological imaging modalities, such as ultrasonography or ultrasound, fluoroscopy, contrast-enhanced imaging, magnetic resonance imaging, tomographic imaging, ionizing radiation imaging, non-ionizing radiation imaging, gamma radiation imaging, positron emission tomography, projection radiography, photoacoustic imaging, tomography, including linear tomography, poly tomography, zonography, orthopantomography, computed tomography with or without enhancement using contrast agent, diffused optical imaging using infrared wavelengths, elastography using ultrasound, MRI, or CT, electrical impedance tomography, as well as optoacoustic imaging.

The imaging can be carried out prior to, during, as well as after the tissue treatment using the energy delivery probe 13. The target tissue 41 can be imaged while the probe is positioned for treatment or adjacent to the site to be treated. This imaging can be used to confirm the correct positioning of the probe, particularly the positioning of the one, two, or more than two voltage delivery regions. Repositioning and reimaging can be carried out until the desired positioning of the probe is achieved. The imaging can provide constant feedback, including real-time feedback, for any portion of, or throughout, the image-guided treatment. The imaging can be used in part to identify the location of the target tissue volume, determine the desired ablation volume for selection of appropriate tissue treatment devices disclosed herein, as well as to identify appropriate point of entry, including puncture, for the probes thereof.

The treatment control module generally applies one test pulse for every pair of electrodes used, although more than one pulse can be applied to each pair. For example, in some embodiments, such as the three probe embodiment illustrated in FIGS. 11A through 11C, there will be three test pulses, one for each pair (1 to 2), (1 to 3), and (2 to 3). The test pulse is completed to diagnostically check the treatment setup before full therapeutic treatment is applied. Each test pulse is intended to ensure that two conditions are met with each test pulse: first, that there is a valid connection between the selected treatment pairs, and second, that the current will not exceed the maximum output capability of the generator 29.

Another reason for the administration of a "test pulse" is to ensure that the patient is properly anesthetized. Prior to treatment, the patient is administered general anesthesia in combination with a paralytic agent or a local anesthetic, such as, but not limited to, muscle blockers like pancuronium. If the patient is not paralyzed with anesthesia, then a noticeable muscle contraction will occur during administration of the "test pulse". Since the test pulse is at approximately 10% to 7% of the therapeutic level, any muscle contraction displayed by the patient is not as much as it would be if full energy was applied. The user should be trained to watch for muscle movement during the test pulse. After these steps are completed, the system charges to the full therapeutic treatment voltage and waits for instructions from the user to begin treatment.

After the treatment has been initiated, the treatment control module controls the generator 29 and administers a series of pulses according to a series of predetermined instructions. The treatment process runs until each step of the probe firing sequence has been accomplished.

The treatment control module can include a feature that prevents the generator 29 from exceeding its maximum current limit by reading the current every ten pulses and reducing the voltage by a predetermined percentage (e.g., 5% or 10%) if it approaches the maximum limit of the generator. The generator 29 can accommodate any number of probes/electrodes (e.g., 6 probes). In the embodiment shown, the pulses can be applied one pair of electrodes at a time, and then switched to another pair.

The system also monitors the current delivered and ensures that for patient safety reasons and for hardware reliability the maximum current capabilities of the system are not exceeded. Low currents can also be detected as a sign of poor connection to the patient. The treatment can either be 1) accepted as is; 2) reduced and reapplied in an automated manner, which will lower the voltage and the corresponding current and will provide some level of treatment; or 3) carried out again by repositioning the probes to be further apart. This will increase the resistance of the system.

After or during the insertion of the energy delivery probe 13 into a patient, other non-limiting treatment method steps described herein can take place in any suitable order of steps, as well as concurrently, without being limited thereto. The methods of the present application can involve providing one or a combination of two or more energy delivery probes 13 disclosed herein that are suitable for ablating at least a portion of the desired ablation volume or its entirety. Criteria for selection of the appropriate energy delivery probes 13 include, but are not limited to, the configuration of the probe and the voltage delivery parameters.

The methods of ablating a target tissue described herein can involve activating the energy source 29. The energy source 29 can be configured to deliver therapeutic energy including high voltage pulses, and can be configured to optionally deliver low voltage testing energy, including low voltage pulses or high voltage pulses or with pulses that are each of a duration shorter than the duration of each therapeutic voltage pulse.

Electrical energy can be delivered from power source 29 through the energy delivery probe device 13 to the target tissue 41 to treat the target tissue. The electrical energy can be delivered to the target tissue 41 in the form of electrical pulses in an amount sufficient to irreversibly electroporate the target tissue 41. Thus, the energy delivery probe 13 of the present application can be capable of delivering electrical pulses to target tissue to cause irreversible electroporation of the identified tissue. The probe 13 can also be used to produce reversible electroporation in certain embodiments to facilitate transportation of macromolecules across membranes, with appropriate modifications in operating parameters. In certain non-limiting examples, the energy delivery probe 13, as described herein, can be used to ablate a predetermined volume of cells in a mammalian subject. Alternatively, the electrical energy can comprise radiofrequency energy.

In one aspect, the energy delivery probe 13 can comprise from about two to about six probe bodies, described below.

One of ordinary skill in the art will recognize that any suitable number of probe bodies can be used in the energy delivery probe 13 described herein. When two or more probe bodies 7, 70 are present in an energy delivery probe 13, or two or more probes of multiple devices are used in combination, the voltage delivery regions of the different probe bodies can be aligned in parallel. In other embodiments, the voltage delivery regions may not be in parallel. The above methods can be applied by persons of ordinary skill in the art to create 3-D treatment zones between exposed portions of electrodes even when the probes are not parallel to each other and even when the amount of the exposed portion varies with each probe.

In one aspect, the voltage delivery region of the second probe body 70 can be positioned such that it is substantially parallel to the voltage delivery region of the first probe body 7. This configuration can help reduce or eliminate the occurrence of electrical shorting and arcing. During use, any two parallel voltage delivery regions of adjacent probes 7, 70 can be energized with the same polarity or opposite polarities. In certain embodiments where multiple probes are utilized together, independently energizing and independently polarizing can be used to ensure current flows from any voltage delivery region on one probe to any voltage delivery region on another probe, at any point along the length of the energy delivery members containing a voltage delivery region.

The details of the treatment parameters can be displayed for a user using the system illustrated in FIG. 7. The firing or switching sequence between probes or energy delivery members can be listed automatically in the window. In the four-probe array configuration, described herein, the firing sequence can involve six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence. Thus, the method described herein can further comprise selecting one of monopolar and bipolar delivery of energy by means of the switching means described above.

In one example, the maximum voltage that can be generated between probes is limited by the capabilities of the generator 29, which in the example is limited to a maximum of 3000 Volts. In one example, the length of each pulse that is generated between energy delivery members 7, 70 during each respective step of the firing sequence can be adjusted. In this example, the pulse length can be predetermined and can be the same for each respective step, and is set at 100 microseconds. In one aspect, a certain number of pulses can be generated and displayed for a user during each respective step of the firing sequence. In the example, the number of pulses can be predetermined and is the same for each respective step, and is set at 90 pulses which are applied in a set of 10 pulses at a time.

In one aspect, the setting for Volts/cm according to the value selected at an input box can be displayed. In one example, the default electric field density setting (Volts/cm) can be shown in the input box. This number represents the electric field density that the user believes is needed to effectively treat the cells, e.g., ablate the tissue cells. For example, 1500 Volts/cm is an electric field density that is needed to irreversibly electroporate the target tissue 41. Based on the number selected in the input box, the treatment control module can automatically adjust the voltage or treatment energy level that is applied between the electrodes. In another aspect, the actual distance between the electrodes, measured in cm, which is automatically calculated according to the placement of each probe in the grid, can be displayed.

The methods of the present application can involve delivering a sufficient number of voltage ablation pulses from the therapeutic energy source 29 through the probe to the target tissue 41. In one aspect, a predetermined voltage can be delivered to the target tissue 41. In one embodiment, the voltage can be 2.5-3 kV, and predetermined electric field strength, including 0.25 kV/cm, 0.425 kV/cm, as well as 0.6 kV/cm. Each of the pulses can have the same or different duration, which can be on the order of 7 microseconds to 70 microseconds, and in certain embodiments can be from 30 microseconds to 100 microseconds. Each of the pulses can have the same or different voltage, which can be of various levels, including, but not limited to 1 kV or greater, 2 kV or greater, 2.7 kV or greater, or 2.5 kV to 3 kV.

Each of the pulses can have the same or different waveforms, such as square, triangle, sawtooth, sine, pulse, composite waveforms, and can be in the form of a Fourier series. Any two consecutive pulses can be separated by an inter-pulse duration of 0.15 seconds or greater, including, but not limited to 0.2 seconds to 1 second or 0.25 seconds to 0.5 seconds. The pulses can be delivered together or separated into subsets of the same or different number of pulses, including, but not limited to subsets of 1 to 10 pulses each. The pulses can be the same or different in pulse duration, waveform, voltage, and amplitude within each subset as well as between different subsets. The ablation treatment that is sufficient to ablate the predetermined ablation volume can require just one pulse or a few pulses if the ablation volume is small, and 10 or more pulses for medium to large ablation volumes, in certain embodiments being 7 or more, 50 or more, 90 or more, 100 or more, 150 or more, 500 or less, 300 or less, or optionally 70 or less.

A "train" is a term used to state a series of sequential electrical pulses. The ablation treatment that is sufficient to ablate the predetermined ablation volume can be delivered within 6 minutes, certain embodiments being 5 minutes or less, or 2 minutes or less, or 1 minute or less. A non-limiting voltage ablation treatment can include multiple trains in one embodiment 9 trains, of multiple pulses, in one embodiment 10 pulses, each, with pulse duration being 100 μs or shorter, pulse waveform being square, duration between consecutive pulses being 0.25 seconds, and duration between consecutive trains being 3 seconds.

In one embodiment, a plurality of sets of pulses can be applied, and more specifically 9 sets of 10 pulses per set can be applied with each pulse having a pulse duration of 100 microseconds. The time between sets of pulses can be about 3.5 seconds and can be a function of how long the capacitors need to charge. In another embodiment, the time between sets of pulses is less than 3.5 seconds or is completely eliminated.

In addition to the example parameters described above, specific electro-medical applications of this technology include reversible electroporation as well as irreversible electroporation. This could include reversible or irreversible damage to the external cell membranes or membranes of the organelles, or damage to individual cellular structures such as mitochondrion so as to affect cellular metabolism or homeostasis of voltage or ion levels. Example embodiments for reversible electroporation can involve 1-8 pulses with a field strength of 1-100 V/cm. Other embodiments altering cellular structure adversely involve generators having a voltage range of 100 kV-300 kV operating with nano-second pulses with a maximum field strength of 2,000V/cm to and in excess of 7,000V/cm between electrodes. Certain embodiments involve between 1-15 pulses between 5 microseconds and 62,000 milliseconds, while others involve pulses of 75 microseconds to 7,000 milliseconds. In certain embodiments the electric field density for the treatment is from 100 Volts per centimeter (V/cm) to 7,000 V/cm, while in other embodiments the density is 70 to 700 V/cm as well as from 300 V/cm to 1000 V/cm. Yet additional embodiments have a maximum field strength density between electrodes of 250V/cm to 500V/cm. The number of pulses can vary. In certain embodiments the number of pulses is from 1 to 100 pulses. In other embodiments, groups of 1 to 100 pulses, or pulse-trains, are applied in succession following a gap of time. In certain embodiments the gap of time between groups of pulses can be between 0.5 second to 10 seconds.

Control of parameters such as pulse durations, inter-pulse durations, voltage, amplitude, pulse waveform, and number of pulses can be controlled by using the therapeutic energy source 29. Such control can be carried out automatically according to preset values, based on at least one sensor, including information from the sensor such as, but not limited to, impedance, current, voltage, chemical concentrations, pH, ionic strength feedbacks, and manual input by the device operator. In certain embodiments, the application of the pulsed electric fields can include pulses of 1.5 kV/cm in 3 trains of 10 pulses each to ablate tissue.

Figure 8D:
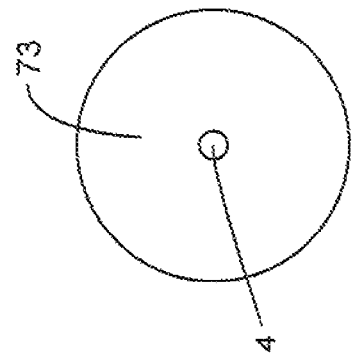
FIG. 8D illustrates a top view of an ablation zone using the device illustrated in FIG. 8A.
Figure 8C:
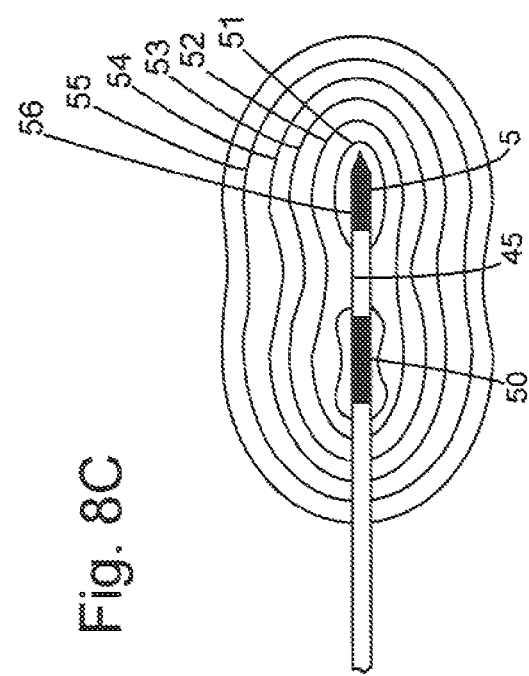
FIG. 8C illustrates a plan view of a pulsed electric field gradient in the form of a Finite Element Analysis (FEA) representation of the energy delivery probe of FIG. 8A in use.

Referring to FIGS. 8C and 8D, the method of ablating a target tissue can involve exposing cells within a predetermined ablation volume to pulsed high intensity electric fields delivered from the energy delivery probe 13. FIGS. 8C and 8D illustrate a plan view and top view of the assembled bipolar probe 13 and an example of the general shape of the treatment zone that can be generated by such a probe type. The plan view shows an example of the general shape of the treatment zone that can be generated by an arrangement of two electrodes 4, 40 separated by an insulation sleeve. The combined electric field gradients resulting from energizing parallel probes can be calculated using finite element analysis (FEA) as described herein. FEA is one accurate numerical model based method for generating a treatment zone between a pair of treatment probes. For example, U.S. Patent Application Publication No. 2007/0043345, which is hereby incorporated by reference, discloses using FEA models to generate treatment zones between a pair of electrodes (the calculations were performed using MATLAB's finite element solver, Femlab v2.2 (The MathWorks, Inc. Natick, Mass.)). The FEA representation shows different patterns that are produced when there are variations in the number of voltage delivery regions as well as when there are differences in lengths or ratios between the voltage delivery regions and the electrically insulating regions.

FIG. 8C illustrates a FEA representation of a pulsed electric field gradient around voltage delivery regions 5, 50 after electrical energy has been delivered through the energy delivery probe 13 illustrated in FIG. 10 to the target tissue 41. Thus, the energy delivery probe 13 described herein can be configured for the delivery of pulsed electric field gradients to target tissue 41 surrounding the two or more voltage delivery regions 5, 50. The electric fields that are produced can cause irreversible electroporation and subsequent cell death of the predetermined ablation volume. The effects of the ablation can be substantially immediately detectable following pulsed voltage ablation delivery.

In one embodiment, the FEA representations that can be used to estimate pulsed voltage ablation volumes and are: 1) outlined by a pulsed voltage ablation threshold of 0.25 kV/cm, 2) estimated by FEA using a 16-gauge, having a diameter of 0.065 inches, probe 13 with different configurations of the voltage delivery regions and the electrically insulating region, and 3) provided by a pulsed voltage of 2.7 kV. In other embodiments, the gauge size can be from 14 gauge to 22 gauge.

The depth of the electric field image can be calculated analytically or with interpolation and displayed on an x-z grid (not shown). Because the distribution of the electric field (i.e., expected treatment region) between two monopolar electrodes may "dip in" along a boundary line, where the width of the region is smaller in the middle, depending on the electrode location and the applied voltage, it is beneficial to have an x-z grid included on the monitor. For example, if this "dip" of the boundary line travels into, rather than surround, the lesion region, then the targeted region may not be fully treated. As a default to ensure treatment of the entire lesion region, the probe depth placement and the exposure length may be set unnecessarily higher to ensure erring on the safe side. However, this will potentially treat a much larger volume than needed, killing healthy surrounding tissue, which can be an issue when treating sensitive tissues such as the pancreas, brain, etc. By optimizing the treatment depth together with the width and height, this effect may be reduced, further enhancing procedural protocol and clinical outcome.

Total treatment volumes, including total ablation volumes, can be identified within the combined electric field gradients, as described herein. Pulsed voltage ablation thresholds, electric field strengths to which cells in a target tissue are exposed substantially damage, destroy, render dead or otherwise metabolically inactivate the cells, can be identified for any tissue type. For example, a pulsed voltage ablation threshold of 0.25 kV/cm has been demonstrated for destruction of certain cancer cells in vitro. This has been discussed in Miller et al., L., Leor J., Rubinsky B. "Cancer Cell[s] Ablation with Irreversible Electroporation." *Technology in Cancer Research and Treatment*, Vol. 4(6), 699-705 (2005), which is hereby incorporated by reference. As such, pulsed voltage ablation volumes of any given configuration of voltage delivery regions can be identified, for example, as the FEA-calculated electric field gradient outlined by a predetermined pulsed voltage ablation threshold (in kV/cm).

As illustrated in FIG. 8C, the pulsed electric field gradients 51 through 56 can radiate away from the energized voltage delivery regions as substantially uniformly gradients of decreasing field strengths. When voltage delivery regions 5, 50 are electrically coupled to voltage pulse source 29, such as a voltage pulse generator, and are oppositely charged, they are capable of providing a pulsed electric field gradient depicted through isometric electric field strength lines 51, 52, 53, 54, 55, and 56, which correspond to electric field strengths of 2.5 kV/cm, 1 kV/cm, 0.425 kV/cm, 0.25 kV/cm, 0.15 kV/cm, and 0.075 kV/cm, respectively. One skilled in the art would understand that the electric field radiates continuously from the voltage delivery regions 5, 50 of probe 13 outward with decreasing field strength, and includes the illustrated isometric electric field strength lines. In certain embodiments of ablation, there is a ratio describing the ablation volume, where the ratio of the diameter to length ablated would be 4:7, such as a diameter of 2 cm and a length of 3.5 cm.

Shapes and sizes of pulsed electric field gradients can depend in part on specific combinations of the following: 1) amplitude of the supplied voltage pulses, 2) dimensions, including lengths as well as diameters, of each of the voltage delivery regions, and 3) dimensions, including lengths as well as diameters, of each of the electrically insulating regions separating the voltage delivery regions.

In certain embodiments, configurations of the voltage delivery regions and the electrically insulating regions can increase or maximize a ratio of diameter to length of the pulsed voltage ablation volume, thereby producing an ablation pattern that is wide and short, or substantially spherical, and can minimize the occurrence of electrical arcing between different voltage delivery regions. This can have broad clinical applications. In certain embodiments, the ratio of diameter to length of the pulsed voltage ablation volume can be 1:2 or greater, and in other embodiments can be 4:7 or greater, and in other embodiments can be 3:5 or greater. In other examples, this ratio of the pulsed voltage ablation volume can be 1:4 or greater, and in other embodiments can have a ratio that is at least one of: 2:7 or greater, 1:3 or greater, as well as 3:7 or greater.

Operating parameters suitable for use with the voltage delivery devices of the present application to ablate selected volumes of tissues using pulsed electric fields include, but are not limited to, amplitude of voltage pulses, duration of each pulse, total number of voltage pulses, and duration between consecutive pulses. Amplitude of voltage pulses can be 1 kV or higher (in certain embodiments being at least one of: 2 kV or higher, 2.5 kV or higher, 2.7 kV or higher, 3 kV or higher, 5 kV or higher).

The duration of each pulse can be about 100 microseconds or shorter, including, but not limited to, 50 microseconds or shorter or alternatively 7 microseconds or shorter. Certain embodiments can include short pulses that would be sufficient to ablate the target tissue 41. Such pulses can include, but are not limited to, a total voltage exposure duration of one second, such as about 10,000 pulses of 100 microseconds each.

In one aspect, the target tissue 41 in the ablation volume subjected to pulsed electric field ablation, as described herein, is, in its entirety, exposed to ablative electric fields at the same time, albeit at different field strengths. Utilizing the electric field application effectively can lead to shortened procedures that can be about 6 minutes or shorter.

In one embodiment, 30 trains of 10 pulses each can be used, with a pulse duration of 100 microseconds, a duration between consecutive pulses of 1 second, and a duration between consecutive trains of 3 seconds. In another embodiment, 300 pulses can be used, with a pulse duration of 100 microseconds and a duration between consecutive pulses of 1 second. In a further embodiment, 9 trains of 10 pulses each can be used, with a pulse duration of 100 microseconds, a duration between consecutive pulses of 0.25 seconds, and a duration between consecutive trains of 3 seconds.

The total number of voltage pulses necessary to ablate a particular cell within a target tissue can depend on cell shape and size within the target tissue, the strength of the electric field the cell is subjected to, and duration of each pulse. In one non-limiting example, a cell requiring a certain number of pulses, for example, 100 pulses of a certain duration, such as 100 microseconds, at a certain field strength, such as 0.4 kV/cm, to be successfully be ablated, can also be ablated when subjected to a smaller number of pulses, such as 60-70 each of substantially the same or shorter duration, such as 7-100 microseconds, at a higher field strength, such as 0.6 kV/cm, or to substantially the same number of pulses, such as 100 each of a shorter duration, such as 7-50 microseconds at substantially the same field strength, such as 0.4 kV/cm.

Referring to FIG. 8D, after the energy delivery probe 13 is inserted into a target tissue 41 and electrical energy is delivered to the tissue, at least a first ablation zone 73 can be produced. The total width of the resulting ablation zone can be about 15 mm. In this embodiment, about 90 pulses of 100 microseconds each at 2.7 kV can be delivered to the target tissue 41. For example, probe 13 of FIG. 8C with a FEA electrical field configuration can generate an ablation volume having a diameter of about 2 cm by a length of about 3.5 cm. For a first cell located at the border of this ablation volume, such as about 1 cm away from probe 13, subjected to a first electric field strength of 0.25 kV/cm during the treatment, all 90 of the pulses can be necessary for ablation of the first cell. However, a second cell within this ablation volume, such as located about 0.5 cm away from probe 13, subjected to a second electric field strength of 1 kV/cm during the treatment, can be ablated with a fewer number of pulses, such as, for example, 40 pulses.

The duration between consecutive pulses can be equal to or longer than the duration of muscle contractions, typically 50-160 milliseconds, to allow muscle cells to substantially recover following each voltage pulse, and to allow substantial dissipation of thermal buildup, it any, as a result of the voltage pulse. Duration between consecutive pulses can be substantially longer than duration of each pulse, such as 2,000-fold or greater. Duration between consecutive pulses can be about 0.15 seconds or longer, or in alternative embodiments, can be about 0.2 seconds or longer, substantially equivalent to a pulse frequency of lower than 5 Hz, or 0.25 seconds or longer, equivalent to a pulse frequency of 4 Hz or lower, or 1 second or longer.

Figure 9:
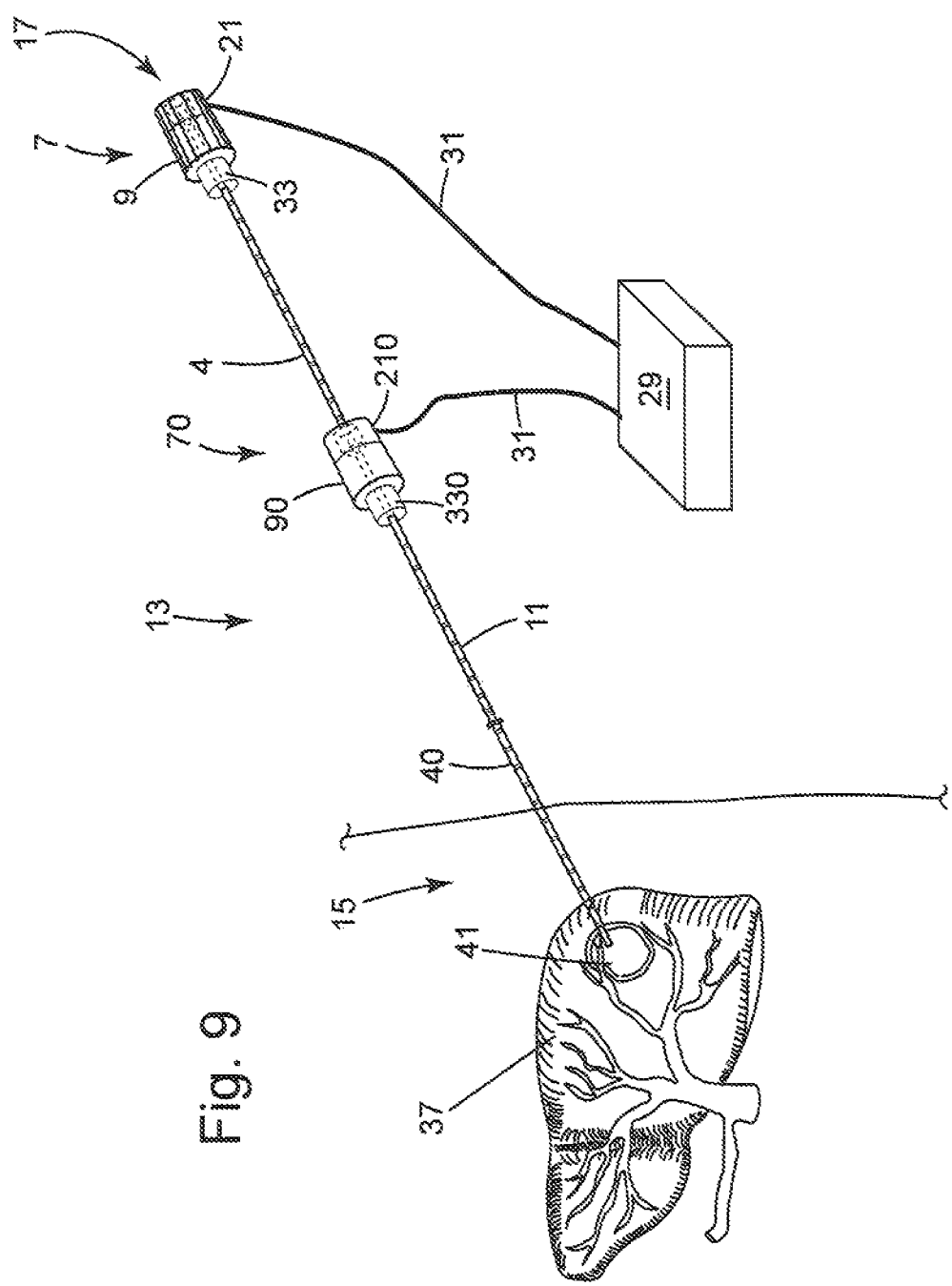
FIG. 9 illustrates a perspective view of a method of use of the energy delivery probe of FIG. 8A.

Referring to FIG. 9, after energy is delivered to a target tissue 41 through the energy ablation device 13, first bipolar ablation of the probe body 7, with corresponding trocar 4, can be removed from probe body 70 and associated cannula 40, while remaining operatively connected to power source 29. The methods of the present application can further involve repeating the steps of inserting and positioning at least a portion of the energy delivery device 13 by delivering therapeutic voltage pulses to produce more than one ablation volume. Subsequent ablation volumes that are produced can overlap, partially overlap, or alternatively, not overlap with the prior ablation volume(s) 73, such that a first ablation zone can overlap with a second ablation zone.

Referring to FIGS. 10A and 10B, after the first probe body 7 and trocar 4 is removed from the second probe body 70, the first probe body and trocar 4 can be repositioned within the target tissue 41 at a desired distance from second probe body 70 and cannula 40, which can remain stationary within target tissue 41, thereby functioning as a fiducial or reference point. The first and second probe bodies can be independently placed to increase the effectiveness of treatment. The first probe body and trocar 4 that is placed in a position relative to the second probe body and cannula 40 can be placed at any desired angle relative to the first electrode 4. In one aspect, the probe body 7 can be inserted into the target tissue 41 such that the first probe body 7 is parallel to the second probe body 70. One of ordinary skill in the art will recognize that the trocar and cannula can be spaced from each other at any suitable distance, depending on the desired ablation zone(s). One of ordinary skill in the art will recognize that other probe placements are possible, and the ablation zone can be adjusted based on the probe placement, as described above. In one aspect, the two or more voltage delivery regions can be positioned at predetermined distances from each other. This can help to decrease the need for ideal probe alignment, accommodate various user skill levels, shorten and simplify the treatment procedure, and increase the reproducibility and reliability of the treatment outcome, such as the size and shape of the ablation volumes.

After the user has placed the probe body(ies) in the patient, distance measurements can be taken. These measurements represent the actual position of the probes in the patient. One way to measure the distances between the probe bodies is to use the imaging device 30 such as an ultrasonic imaging device which allows the user to select any two point on the display device 31 to automatically measure the distance as is well-known in the art.

In some cases, it can be difficult for a practitioner to physically place the probe bodies at the same location(s) shown on the grid. For example, certain anatomical structures of the patient may prevent the optimal placement of the energy delivery probe 13, e.g., the location of the lesion with respect to the location of a patient's ribs, etc.

To address this problem, a user can click on a "Probe Distance Adjuster" button or the like on the screen. As discussed above, the user can select which probes to "lock" on the grid 70, which will fix the location of those probes relative to the grid. After the measurement distances have been inputted, the user can click on the "OK" button to execute this automatic probe placement feature.

The treatment control module can then automatically adjust the placement of the probes on the grid which have not been "locked" to best match the distance measurements taken. By adding an additional diagonal treatment, overlapping with the other treatment zones, in combination with other edits, as described above, the user can tailor the shape of the combined treatment region.

Electrical energy can again be delivered from the power source 29 through at least one of the first energy delivery member 4 and the second energy delivery member 40 to deliver electrical energy to the target tissue 41. In this separated position, trocar 4 and cannula 40 can function as a pair of independent monopolar IRE electrode probes. The monopolar energy delivery involves the ablation or other treatment of tissue through the application of energy from energy delivery members 7, 70, each containing a single voltage delivery region 5, 50. Thus, together the trocar 4 and the cannula 40 can be used as a bipolar device, and when they are separated, as shown in FIGS. 10A and 10B, they can be used as monopolar devices.

The methods described herein, as illustrated in FIG. 10C, can be used to achieve a larger ablation zone(s) compared to the ablation zone 73 illustrated in FIG. 8D. Each of the above-described methods determines a boundary line surrounding a treatment zone that is created between a pair of electrodes 4, 40. By combining a plurality of ablation zones with each ablation zone being defined by a pair of electrodes, a combined treatment region can be displayed on an x-y grid (not shown). FIG. 10C illustrates a top view of the two probe configuration and an example of the general shape of the treatment zone that can be generated by such a two probe configuration, as illustrated in FIG. 10A. The circles within the ablation volume 73 represent the first and second electrodes 4, 40. In one aspect, the probes 7, 70 can be spaced about 15 mm apart. The total width of the resulting ablation zone can be about 25 mm. As described above, one of ordinary skill will recognize that the volume of the ablation zone 73 can be adjusted based on the relative positions of the trocar 4 and the cannula 40. The volume 73 can be adjusted by varying the sizing, the positioning, and the spacing of the electrodes 4, 40, the voltage, and the pulse parameters, as described herein.

The energy delivery probe device 13 and method of use described herein is advantageous because the device can be manufactured using one model or stock-keeping unit (SKU) number to produce multiple polarity devices. The probe device 13 also combines the features of single and bipolar probe electrodes and allows multiple tissue ablation zones to be created while allowing a user to maintain at least one fiducial point in the target tissue 41 by leaving the cannula 40 at the initial treatment point. This minimizes treatment disruption and enhances the overall efficiency and efficacy of the ablation procedure. The energy delivery probe 13 described herein is advantageous because it can be used for RF or IRE ablation, so it can be a dual mode, dual function, i.e., a bipolar and/or monopolar mode.

During the method of use of this device, the placement of the first electrode 4 in relation to the second electrode 40, as well as the distance and angles between the second electrode and the first stationary electrode or fiducial can be measured and/or adjusted in order to produce a desired ablation zone. The mobility of one electrode or trocar 4 in relationship to another electrode or cannula 40 allows a practitioner to change the position and angle between the two electrodes and to produce various sized desired ablation zones. As described above, the stationary electrode 4 could function as the fiducial and can also serve as a treatment marker. The stationary electrode or fiducial can serve as a reference point for further positioning of the electrodes 40, 400, and so on, and can help a user to adjust the ablation zones, as needed. In other embodiments, the electrode 4 can be used as a fiducial to perform a biopsy. The fiducial can be used as a marker or reference point for a first delivery of electrical pulses. The second electrode 40 can be removed, reinserted into the target tissue 41, and positioned at a desired distance from the first electrode 4.

Figure 11A:
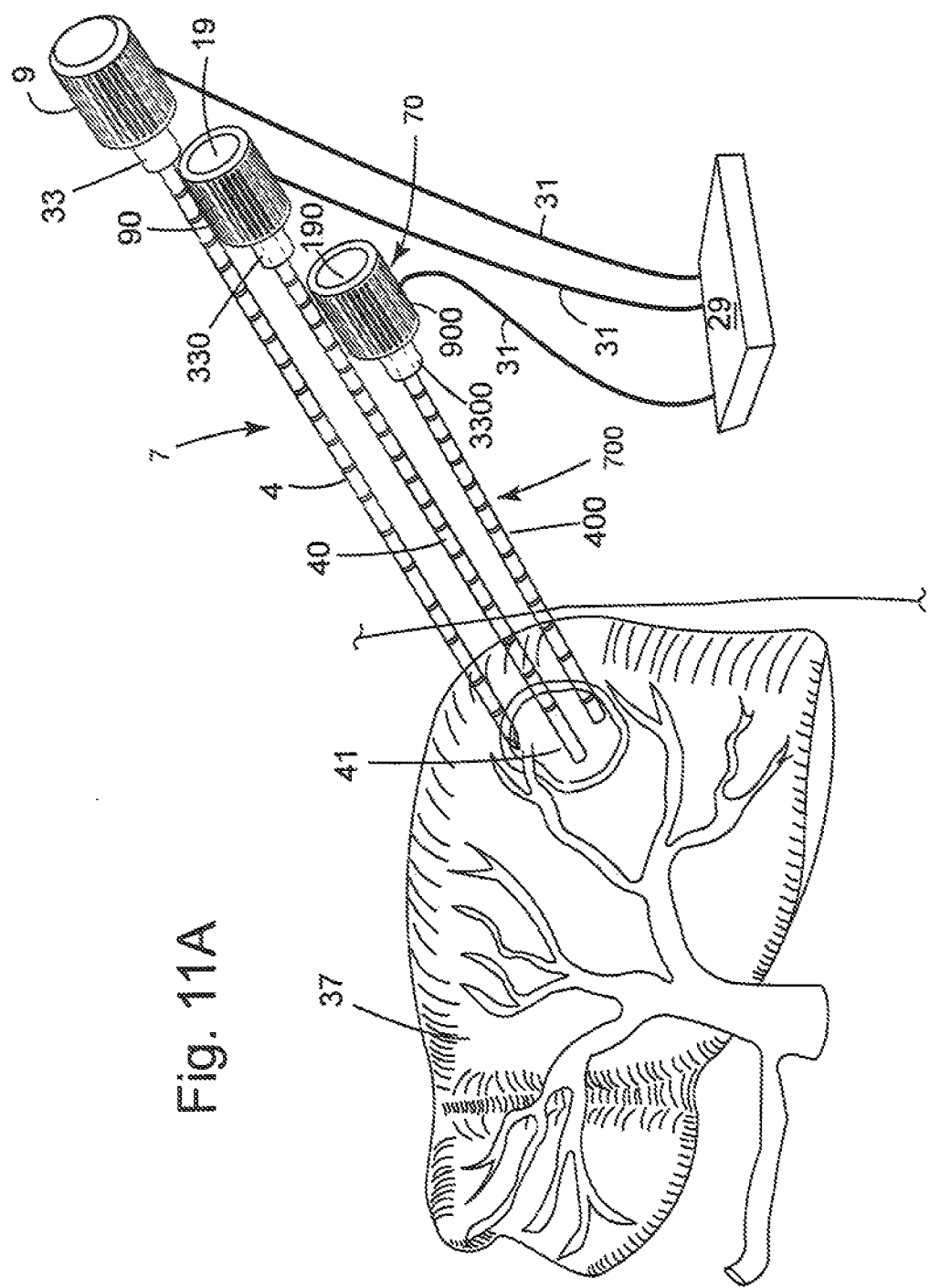
FIG. 11A illustrates a method of treatment using the energy delivery probe illustrated in FIG. 6A.
Figure 11C:
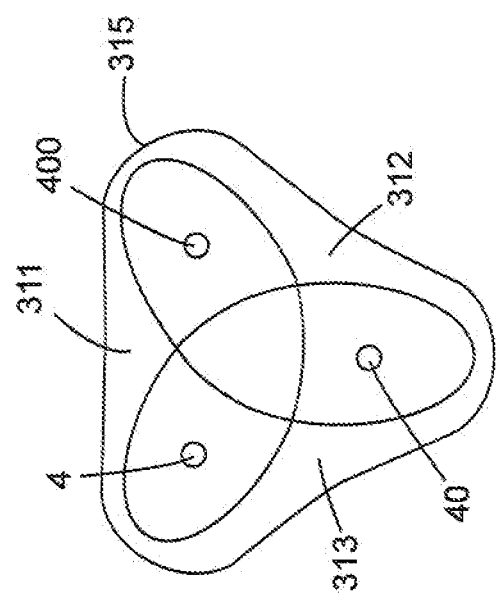
FIG. 11C illustrates a top view of an ablation zone produced by the energy delivery probe of FIG. 11A.
Figure 11B:
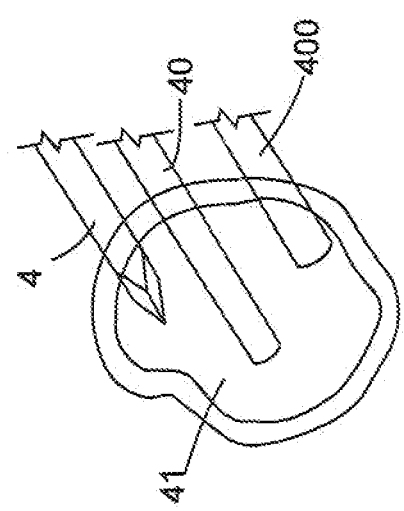
FIG. 11B illustrates an enlarged view of the distal ends of the energy delivery probes of FIG. 11A inserted into a target tissue.

Referring to FIGS. 11A and 11B, three different probe bodies 7, 70, 700 can be used to perform an ablation. In this example, the probe bodies 7, 70, 700, also illustrated in FIG. 6A, can be initially inserted and positioned into a target tissue 41 in an interlocked position as one device. The first probe body 7 can be removed from the second probe body 70 and inserted into a target tissue 41, as described above. The second probe body 70 can be removed from the third probe body 700 and inserted into a target tissue 41 in the same manner. The third probe body 700 can be positioned a predetermined distance from the first probe body 7 and the second probe body 70 to produce a desired ablation zone, illustrated in FIG. 11D, for example.

FIGS. 11C and 11D illustrate a side view and top view of the three probe configuration illustrated in FIG. 11A and an example of the general shape of the treatment zone that can be generated by the three probe configuration. FIG. 11C shows a pattern resulting from the presence of three voltage delivery regions, where each of the distal voltage delivery regions 5, 50, 500 are separated by intervening electrically insulating regions. FIG. 11C is a further FEA representation of a pulsed electric field gradient around voltage delivery regions. Three voltage delivery regions 5, 50, and 500, are separated from each other by two electrically insulating regions 45, 450 of substantially equal lengths. When voltage delivery regions 5 and 50 are electrically coupled to a voltage pulse source, such as a voltage pulse generator, and are charged oppositely to voltage delivery region 500, with a voltage difference of 3 kV, they are capable of providing a pulsed voltage gradient where the ablation volume achievable can extend from the probe out to line 56 in the pattern of line 56. Isometric electric field strength lines 51, 52, 53, 54, 55, and 56 correspond to electric field strengths of 2.5 kV/cm, 1 kV/cm, 0.425 kV/cm, 0.25 kV/cm, 0.15 kV/cm and 0.075 kV/cm, respectively. One skilled in the art would understand that voltage gradients radiate continuously from the voltage delivery regions of probe 13 outward with decreasing field strength, and includes the illustrated isometric electric field strength lines. In certain embodiments the ablation volume can be seen with a bulging section a voltage delivery region.

Voltage delivery regions 5, 50, 500 can be independently polarized as well as independently energized to ensure that a circuit is formed for current movement from any one of the voltage delivery regions to any other of the voltage delivery regions. In certain embodiments a cathodic polarization in the voltage delivery region including the tip 23, at the distal end of the probe 13, can be energized such that current can flow from the tip 23 to a voltage delivery region independently charged anodically that is not at the tip 23 and is closer to the proximal half of the probe 13, closest to the distal portion of the handle 9, than to the tip 23. In certain embodiments where multiple probes are utilized together, either monopolar, bipolar, or a combination of monopolar or bipolar, the voltage delivery regions can be independently energized and independently polarized and can be used to ensure current flows from any voltage delivery region on one probe 7 to any voltage delivery region on another probe 70, at any point along the length of the energy delivery members containing a voltage delivery region.

FIG. 11D illustrates three electrodes 4, 40, 400 defining three individual treatment zones 311, 312, 313, which combine to form an exemplary combined treatment region 315 which is shown with hatched lines. In one aspect, as illustrated in FIG. 11D, a triangular shaped ablation can be produced by the positioning of the probes in a triangular placement. In the illustrated example, the exposed portion of each of the electrodes as shown can be 7 mm in length and each pair of the three probes are equally spaced from each other by 15 mm, as measured at three places, meaning that there are three pairs (pairs 1-2, 2-3 and 1-3) where the spacing is equal to 15 mm. In one aspect, the resulting ablation zone can be about 25 mm in width by about 26.5 mm in height.

Figure 12A:
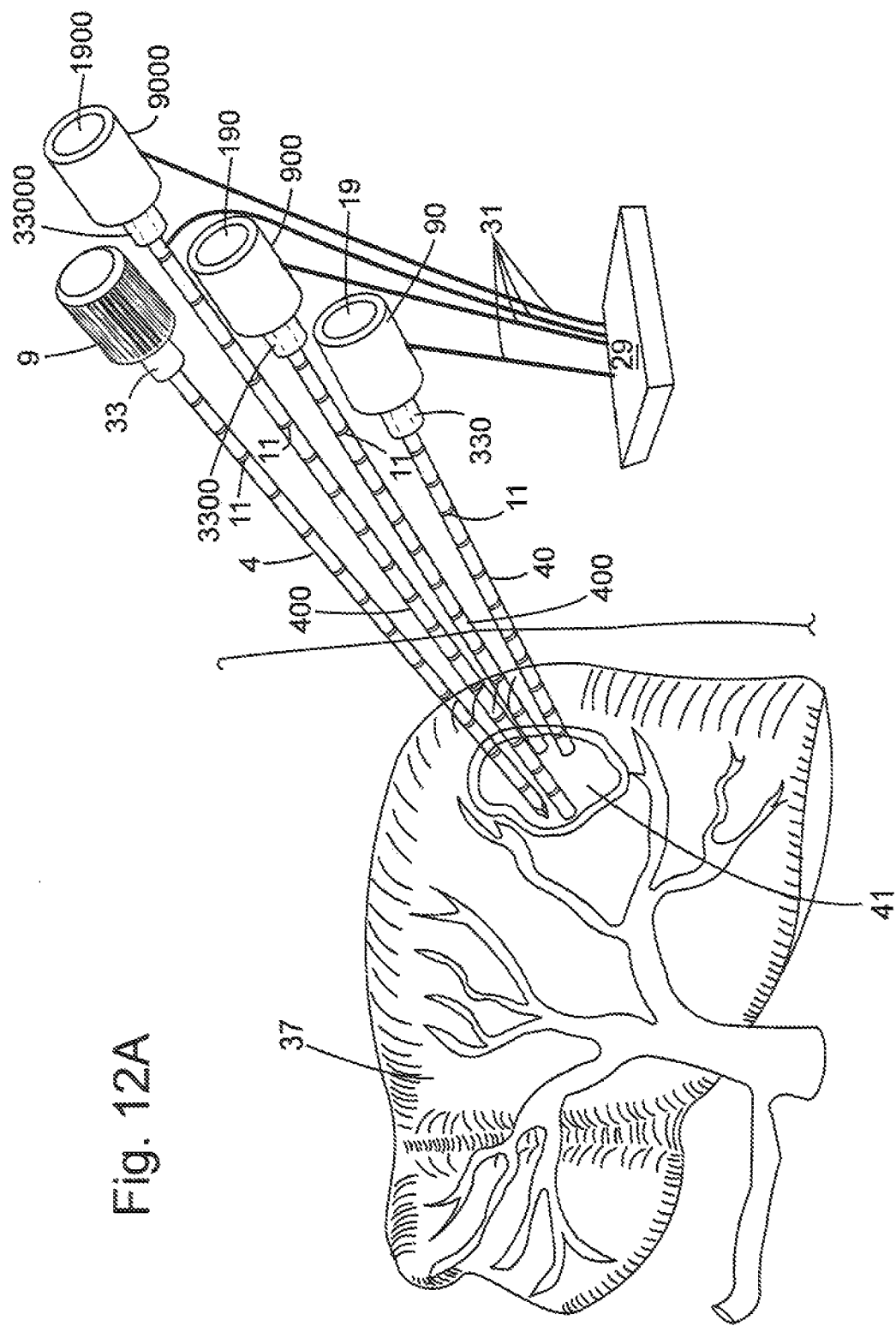
FIG. 12A illustrates a method of treatment using an energy delivery probe having four energy delivery members.

Referring to FIGS. 12A and 12B, in this embodiment, four different probe bodies can be used to perform an ablation. In this example, the probes 7, 70, 700, 7000, can be initially inserted and positioned into a target tissue 41 in an interlocked position as one device. The first probe body 7 can be removed from the second probe body 70 and inserted into a target tissue 41 at a distance from the first probe 7, as described above. The second probe body 70 can be removed from the third probe body 700 and inserted into a target tissue 41 in the same manner such that the second probe 70 is positioned at a distance from the first and second probe bodies 7, 70. Finally, the fourth probe body 7000 can be positioned from the first, second, and third probe bodies 7, 70, 700, such that the position of the probes 7, 70, 700, and 7000 relative to each other can produce a desired ablation zone. The probes can be positioned in any desired distance from each other to produce the desired ablation zones.

FIG. 15C illustrates a top view of the four probe array and an example of the general shape of the treatment zone that can be generated by a four probe array. In this embodiment, each probe can be individually placed into the target tissue 41 such that each probe is parallel and spaced in a substantially square configuration. FIG. 15C shows a pattern resulting from the presence of four voltage delivery regions 5, 50, 500, 5000, where each voltage delivery region is separated by an insulating region. In the illustrated example, the exposed portion of each of the electrodes as shown can be 7 mm in length, and each pair of the four probes can be equally spaced from each other by 15 mm, as measured at four places along the perimeter.

Each of the four probe bodies 7, 70, 70, 700, 7000 can be displayed in the grid, and each probe can be manually positioned within the grid by clicking and dragging the probe with a pointing device 14. In some embodiments, at least one fiducial can be used as a point of reference. The fiducial can be at least one of the probe bodies. In other embodiments, the fiducial can be a non-probe body. Two fiducials (not shown) can be displayed on the grid and can be used as a point of reference or a measure. In the four-probe array configuration, described herein, the firing sequence can involve six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence.

After delivery of electrical energy, such as, but not limited to electrical pulses to the target tissue 41, the methods of the present application can involve terminating the delivery of voltage ablation pulses based on predetermined criteria as well as based on feedback signals. Feedback signals can include sensor feedback signals, visual confirmation of predetermined desirable changes by the operator, or combinations thereof.

The methods of the present application can further involve retracting the probes partially or fully from the subject once all selected treatment volumes are treated. The probe track can be cauterized as understood by one of ordinary skill in the art, if desired.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodiments described herein, which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions can be provided by alternative embodiments without departing from the scope of the appended claims. In this regard, for example, different combinations of elements and/or functions than those explicitly described above are also contemplated as can be set forth in some of the appended claims.

This completes the description of the selected embodiments of the invention. Those skilled in the art can recognize other equivalents to the specific embodiments described herein which equivalents are intended to be encompassed by the claims attached hereto.

What is claimed is:

1. A method of ablating tissue comprising:
   identifying a tissue to be ablated;
   choosing a probe type configuration prior to treatment, the probe type configuration comprising at least one energy delivery probe;
   displaying a placement of the at least one energy delivery probe relative to the identified tissue shown on a display unit;
   inserting at least a portion of the at least one energy delivery probe into the identified tissue, the energy delivery probe including a first energy delivery member having a first handle member and a second energy delivery member having a second handle member positioned along a longitudinal axis, each handle member having a proximal end and a distal end, wherein at least a portion of the distal end of the first handle member is coupled to at least a portion of the proximal end of the second handle member, the first energy delivery member and the second energy delivery member being individually activatable;
   delivering electrical energy through the at least one energy delivery probe to the identified tissue in an amount sufficient to irreversibly electroporate the identified tissue such that at least a first ablation zone is formed;
   removing the first energy delivery member from the second energy delivery member after the electrical energy has been delivered through the energy delivery probe, the second energy delivery member remaining within the identified tissue; and
   re-inserting at least a portion of the first energy delivery member into the identified tissue such that the first and second handle members are spaced horizontally from each other; and
   delivering electrical energy through at least one of the first and second energy delivery members to the identified tissue in an amount sufficient to irreversibly electroporate the identified tissue such that at least a second ablation zone is formed.

2. The method of claim 1, wherein the second delivering step includes ablating the identified tissue such that at least a portion of the first ablation zone overlaps at least a portion of the second ablation zone.

3. The method of claim 1, wherein the first delivering step includes delivering at least one of bipolar electrical energy and monopolar electrical energy.

4. The method of claim 1, wherein the first delivering step includes switching between delivery of bipolar energy and monopolar energy.

5. The method of claim 1, further comprising inserting fluid into the identified tissue through the at least one energy delivery probe.

6. The method of claim 1, further comprising inputting dimensions of the identified tissue into a treatment control computer, the treatment control computer being in communication with the display unit, the dimensions of the identified tissue being shown on the display unit.

7. The method of claim 1, wherein the step of inserting comprises inserting at least a portion of the at least one energy delivery probe percutaneously, laparoscopically, or endoscopically.

8. A method of ablating tissue comprising:
identifying a tissue to be ablated;
inserting an energy delivery probe into the identified tissue, the energy delivery probe including an elongated outer delivery member having a first handle member and at least one electrode adapted to be in contact with tissue and an elongated inner delivery member having a second handle member and at least one electrode adapted to be in contact with tissue and being removably received in the outer delivery member while the outer delivery member remains within the identified tissue, the inner delivery member having a tissue piercing distal end, the outer delivery member and the inner delivery member being individually activatable;
delivering electrical energy through the inserted electrodes of the inner and outer delivery members to the identified tissue to irreversibly electroporate at least a portion of the identified tissue, the delivery of electrical energy comprising at least one pulse train comprising a first set of five pulses in either positive or negative polarity, a first delay of up to 2 seconds, a second set of five pulses in the opposite polarity as the first set of five pulses, and a second delay of at least 3.5 seconds;
removing the inner delivery member from the outer delivery member after the electrical energy has been delivered;
re-inserting the inner energy delivery member into the identified tissue outside of the outer delivery member such that the first and second handle members are spaced horizontally from each other; and
repeating the pulse train after the second delay.

9. The method of claim 8, wherein the second delivering step of repeating includes delivering electrical energy through the electrodes of the inner and outer delivery members to the identified tissue.

10. The method of claim 8, wherein the delivering step includes delivering bipolar electrical energy.

11. The method of claim 8, wherein the delivering step includes delivering both bipolar energy and monopolar energy.

12. The method of claim 8, wherein the step of repeating the pulse train further comprises repeating until a predetermined ablation volume is achieved.

13. The method of claim 12, wherein the step of repeating the pulse train further comprises repeating the pulse train for up to 6 minutes.

14. The method of claim 8, wherein the step of inserting comprises inserting at least a portion of the at least one energy delivery probe percutaneously, laparoscopically, or endoscopically.

* * * * *